(12) United States Patent
Carol et al.

(10) Patent No.: US 6,393,096 B1
(45) Date of Patent: May 21, 2002

(54) PLANNING METHOD AND APPARATUS FOR RADIATION DOSIMETRY

(75) Inventors: Mark P. Carol; Robert Hill; Bruce H. Curran; Richard Nash, all of Sewickley, PA (US)

(73) Assignee: Nomos Corporation, Sewickley, PA (US)

(*) Notice: Subject to any disclaimer, the term of this patent is extended or adjusted under 35 U.S.C. 154(b) by 0 days.

(21) Appl. No.: 09/320,980

(22) Filed: May 27, 1999

Related U.S. Application Data

(60) Provisional application No. 60/087,049, filed on May 27, 1998.

(51) Int. Cl.$^7$ ................................................. A61N 5/10
(52) U.S. Cl. ........................................ 378/65; 378/151
(58) Field of Search ............................ 378/64, 65, 108, 378/151

(56) References Cited

U.S. PATENT DOCUMENTS

| | | | |
|---|---|---|---|
| 5,027,818 A | | 7/1991 | Bova et al. |
| 5,317,616 A | | 5/1994 | Swerdloff et al. |
| 5,351,280 A | | 9/1994 | Swerdloff et al. |
| 5,379,333 A | | 1/1995 | Toth |
| 5,394,452 A | | 2/1995 | Swerdloff et al. |
| 5,400,378 A | | 3/1995 | Toth |
| 5,511,549 A | | 4/1996 | Legg et al. |
| 5,513,238 A | | 4/1996 | Leber et al. |
| 5,596,619 A | | 1/1997 | Carol |
| 5,602,892 A | | 2/1997 | Llacer |
| 5,647,663 A | | 7/1997 | Holmes |
| 5,782,739 A | * | 7/1998 | Criss et al. ................. 600/1 |
| 5,802,136 A | | 9/1998 | Carol |
| 5,818,902 A | * | 10/1998 | Yu ............................ 378/65 |
| 6,038,283 A | * | 3/2000 | Carol et al. ............... 378/65 |

FOREIGN PATENT DOCUMENTS

| | | |
|---|---|---|
| EP | 0 560 331 A1 | 9/1993 |
| EP | 0 695 560 A3 | 2/1996 |
| WO | WO 90/14129 | 11/1990 |

OTHER PUBLICATIONS

"Wedge–Shaped Dose Distributions By Computer–Controlled Collimator Motion"; Kijewski et al.; Med. Phys., vol. 5, Sep./Oct. 1978; pp. 426–429.

"Dosage Calculations in Radiation Therapy"; Urban & Schwarzenberg, 1979; W.L. Saylor and T. Ames; pp. 19–34.

"Treatment Plan Optimization For Conformal Therapy"; I. Rosen and R. Lane; pp. 357–360; The Use of Computers in Radiation Therapy, 1987.

(List continued on next page.)

Primary Examiner—David V. Bruce
(74) Attorney, Agent, or Firm—Bracewell & Patterson, L.L.P.

(57) ABSTRACT

A method and apparatus for determining an optimized radiation beam arrangement for applying radiation to a tumor target volume while minimizing radiation of a structure volume in a patient, comprising: using a computer to computationally obtain a proposed radiation beam arrangement; using the computer to computationally change the proposed radiation beam arrangement iteratively, incorporating a cost function at each iteration to approach correspondence of a CDVH associated with the proposed radiation beam arrangement to a CDVH associated with a predetermined desired dose prescription; comparing the dose distribution to a prescribed dose for the tumor volume and surrounding tissue structures, and increasing or decreasing radiation beam intensity if the change of the proposed beam arrangement leads to a greater correspondence to the desired dose prescription to obtain an optimized radiation beam arrangement.

46 Claims, 11 Drawing Sheets

OTHER PUBLICATIONS

"Shaping of Arbitrary Dose Distributions by Dynamic Multileaf Collimation"; P. Kallman et al.; Phys. Med. Biol., 1988, vol. 33, No. 11, pp. 1291–1300.

"Computer–Assisted Conformation Radiotherapy With a Variable Thickness Multi–Leaf Filter"; Kobayashi et al.; I. J. Radiation Oncology Biology Physics, Jun. 1989, vol. 16, pp. 1631–1635.

"Optimisation of Conformal Radiotherapy Dose Distributions by Simulated Annealing"; S. Web; Phys. Med. Biol. 1989, vol. 34, No. 10, pp. 1349–1370.

"Radiation Phyics"; F. Bova; Stereotacit Neurosurgery; Neurosurgery Clinics of North America, vol. 1, No. 4, Oct. 1990, pp. 909–931.

"Optimization of Conformal Radiotherapy Dose Distributions by Simulated Annealing: 2. Inclusion of Scatter in the 2D Techinque"; S. Webb; Phys. Med. Biol. 1991, vol. 36, No. 9, pp. 1227–1237.

"Optimization by Simulated Annealing of Three–Dimensional Conformal Treatment Planning for Radiation Fields Defined by a Multileaf Collimator"; S. Webb; Phys. Med. Biol. 1991, vol. 36, No. 9, pp. 1201–1226.

"Algorithm for Dosimetry of Miltiarc Linear–Accelerator Stereotactic Radiosurgery"; Luxton et al.; Medical Physics, vol. 18, No. 6, Nov./Dec. 1991, pp. 1211–1222.

"The Generation of Intensity–Modulated Fields for Conformal Radiotherapy by Dynamic Collimation"; D. Convery and M. E. Rosenbloom; Phys. Med. Biol., 1992, vol. 37, No. 6, pp. 1359–1374.

"Intensity Modulated Radiation Therapy May Improve Tumor Control & Decrease Complications," Advance for Administrators in Radiology, Radiology Technology Profile, Jul. 1996.

"Design and Delivery of Intensity–Modulated Profiles in Radiation Therapy"; S. V. Spirov; UMI Dissertation Services, Available to Public Mar. 1977.

* cited by examiner

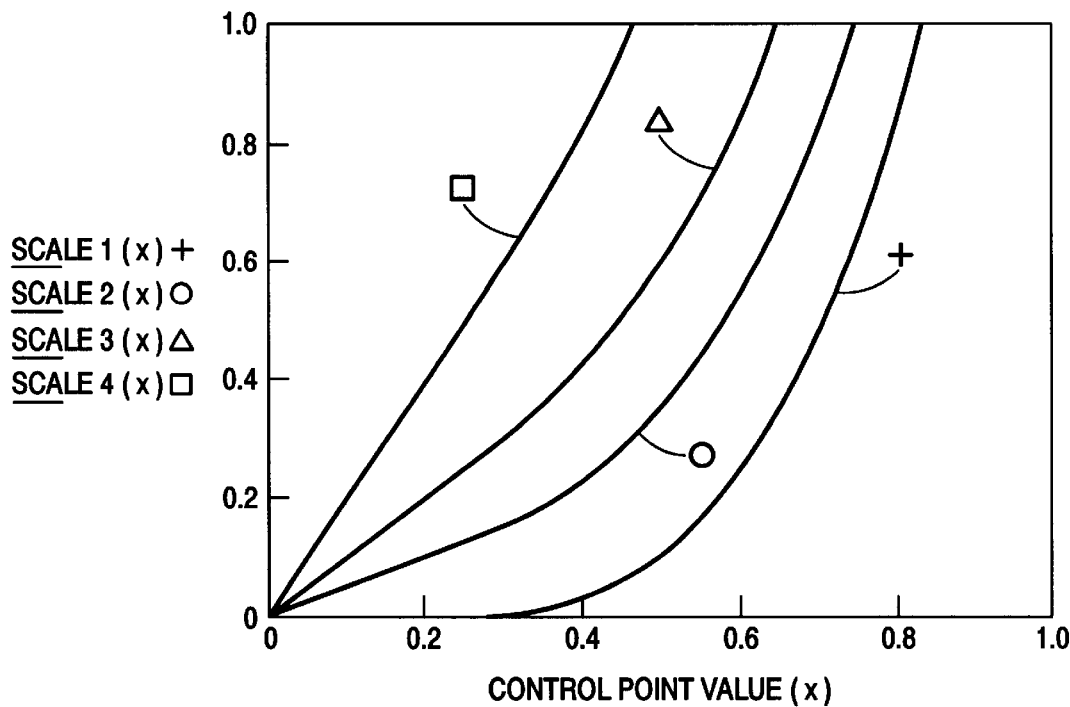
FIG. 7A  SCALE CHANGE ABSOLUTE
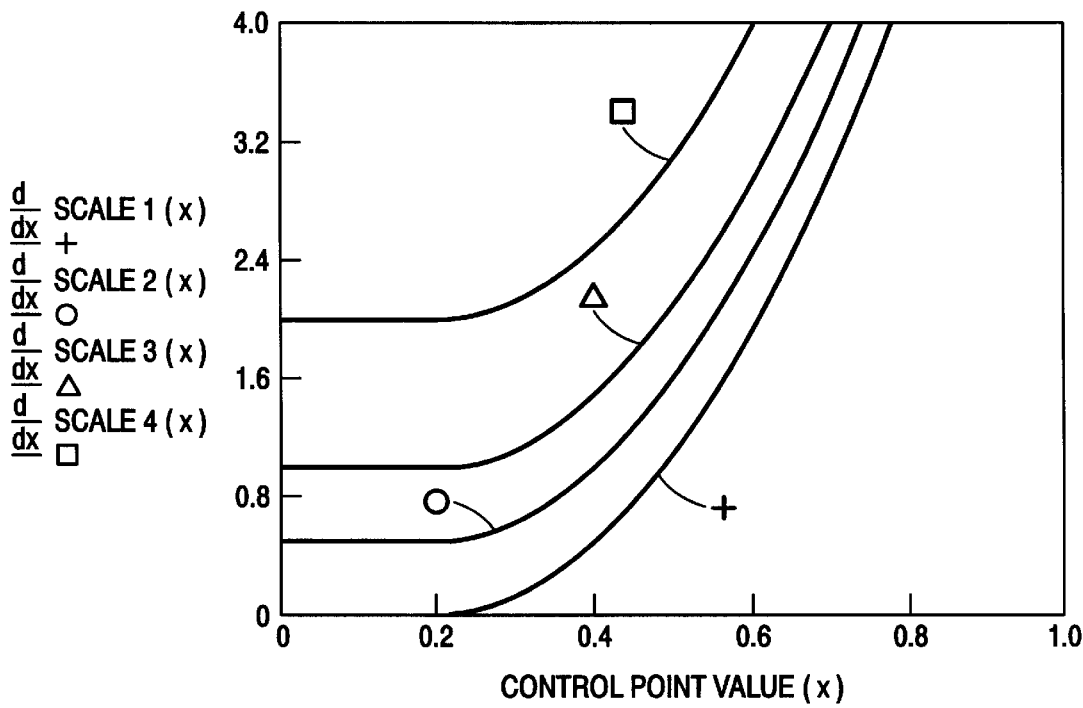
FIG. 7B  SCALE CHANGE SLOPE

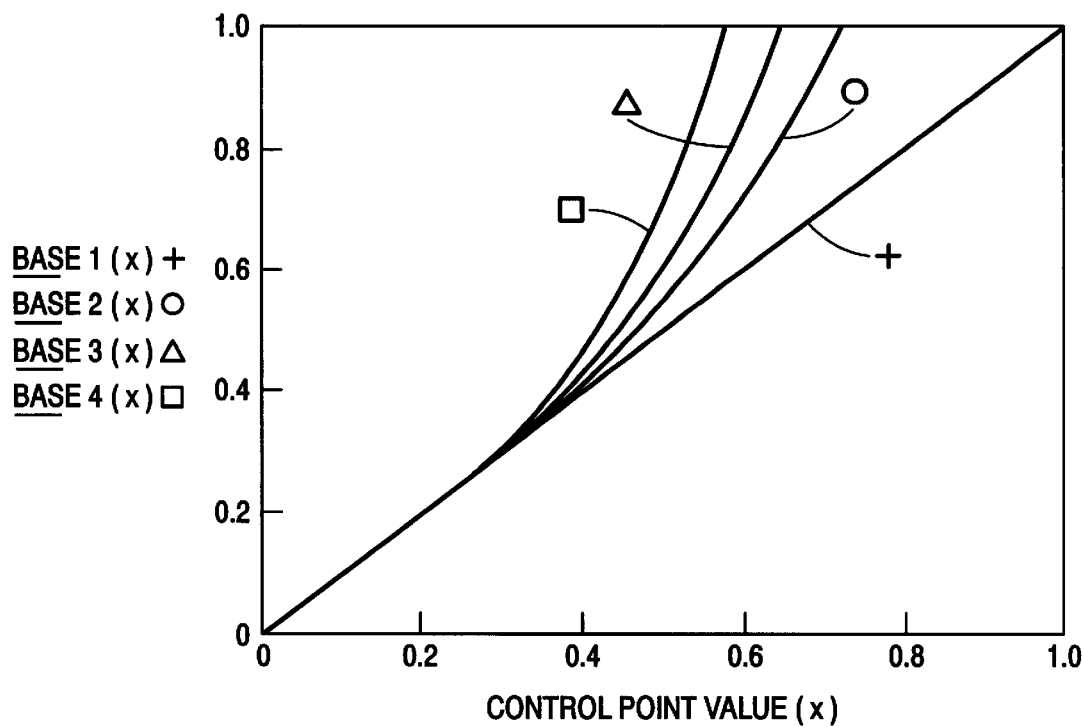
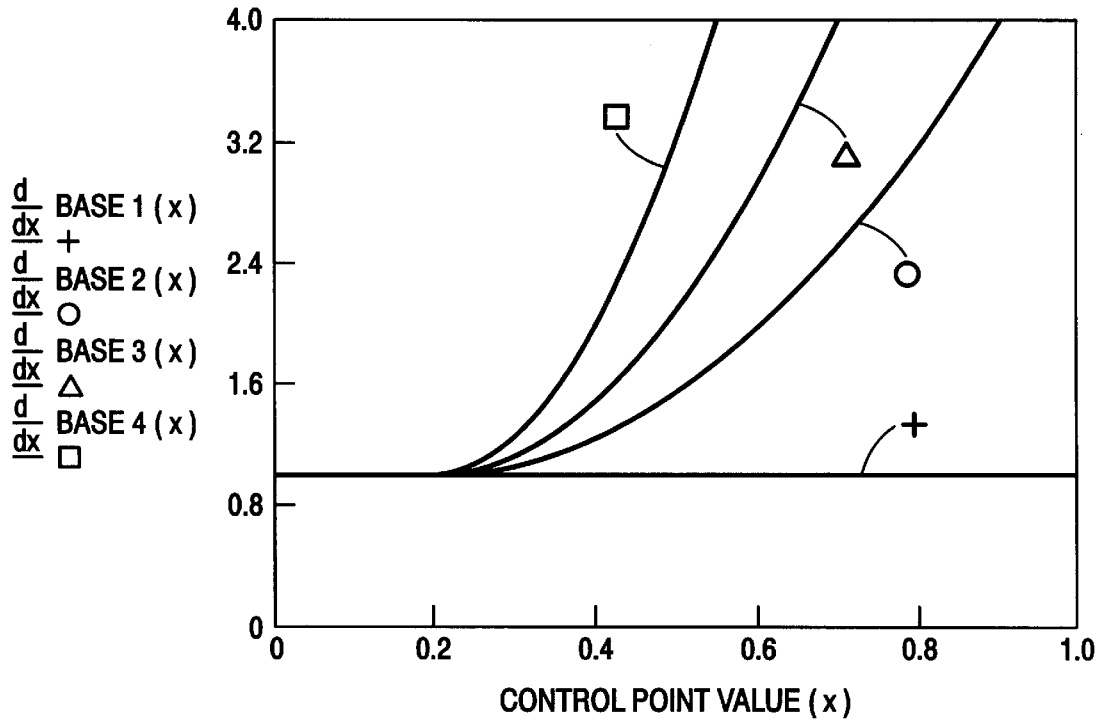

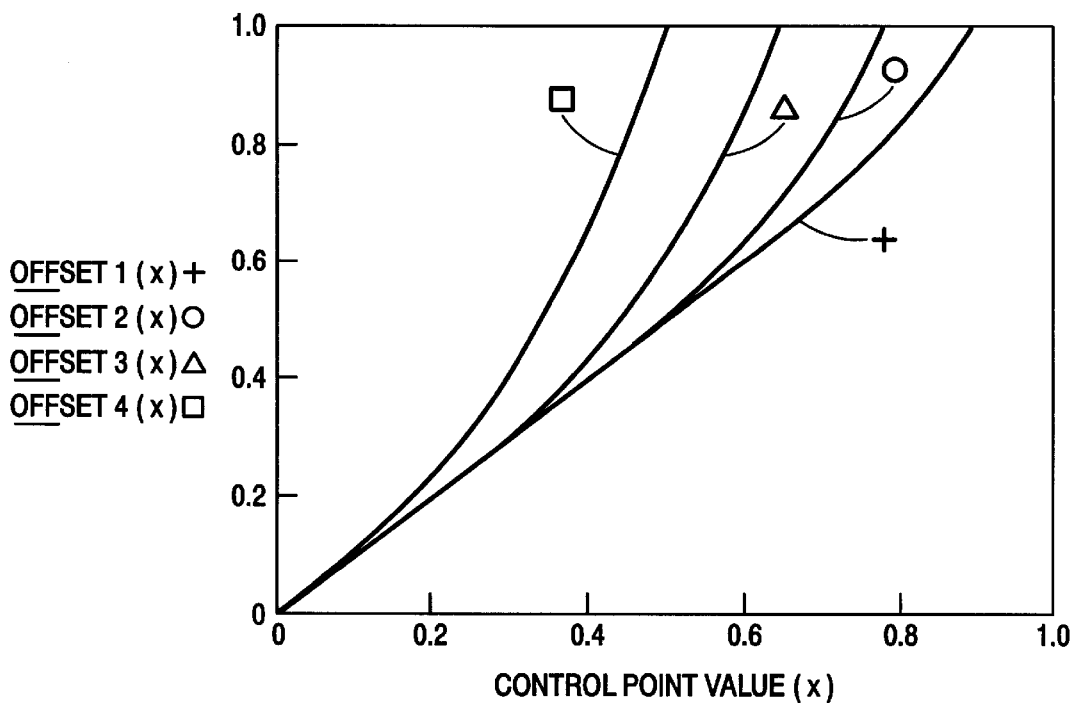
FIG. 7E OFFSET CHANGE ABSOLUTE
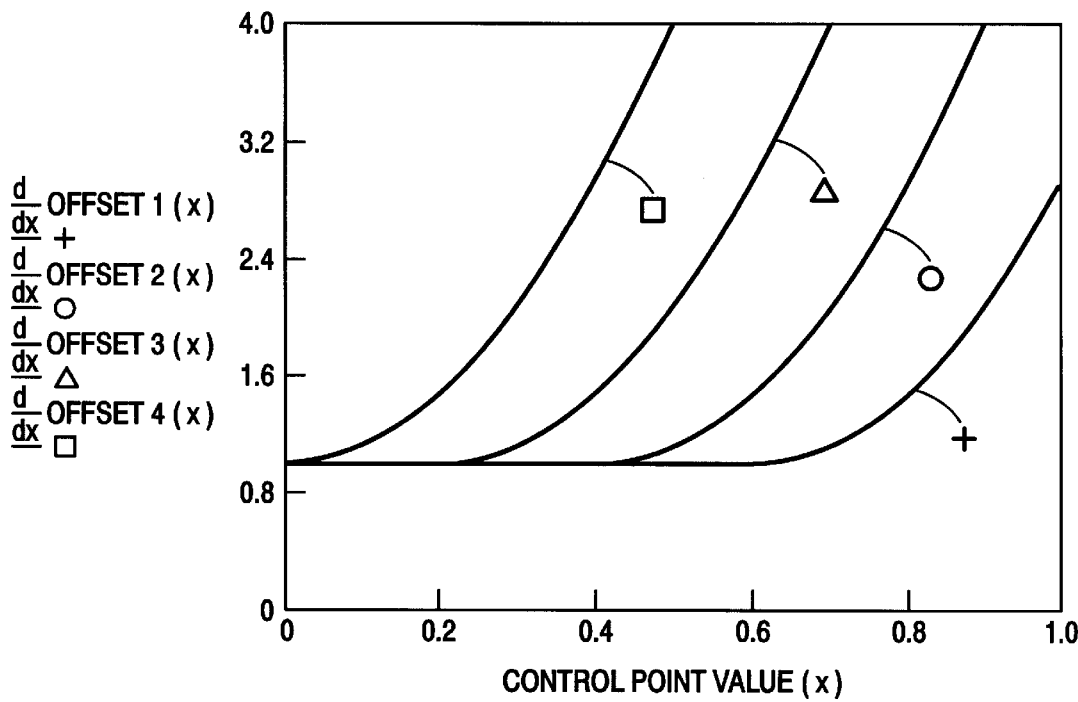
FIG. 7F OFFSET CHANGE SLOPE

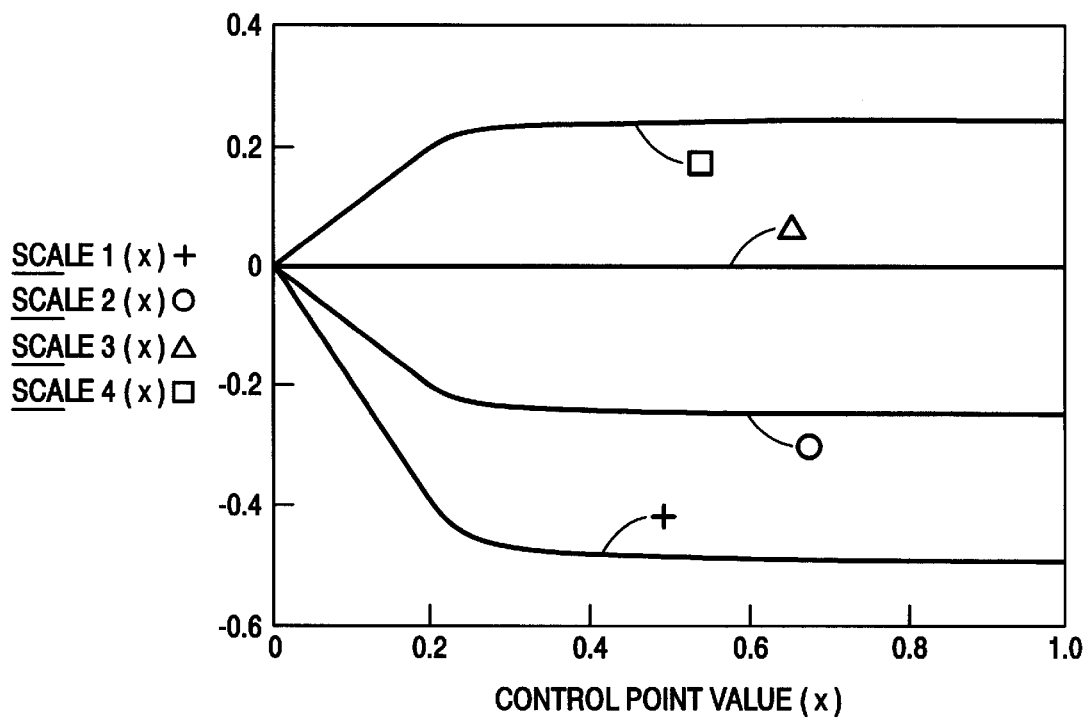
SCALE CHANGE ABSOLUTE FIG. 8A
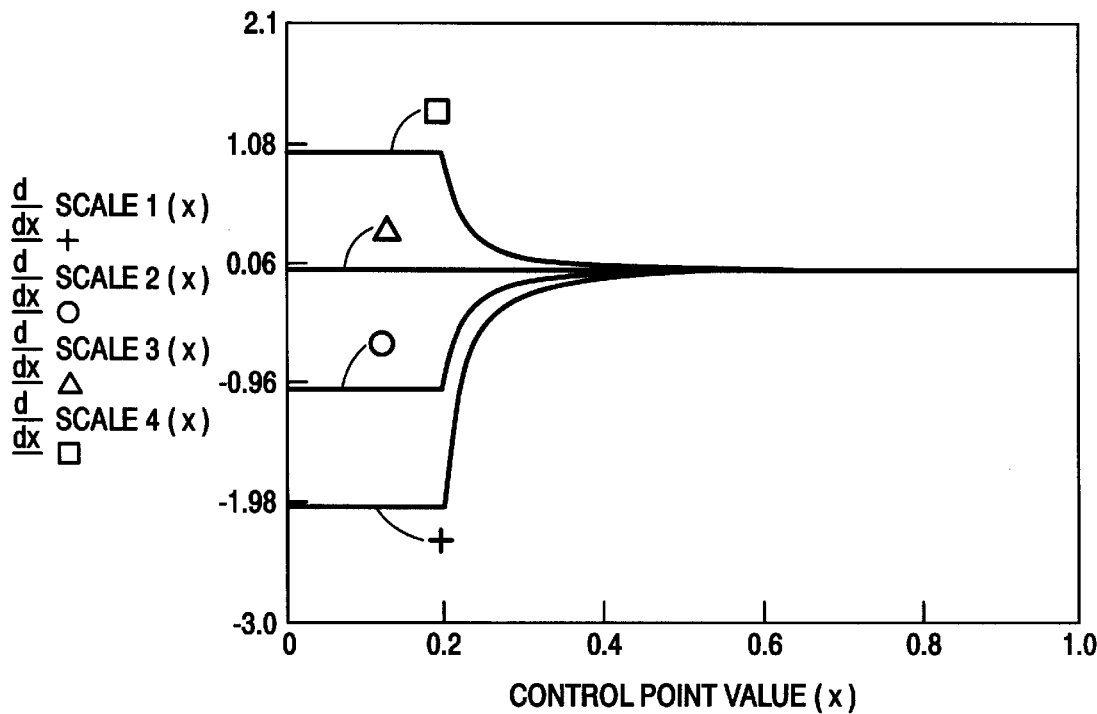
FIG. 8B SCALE CHANGE SLOPE

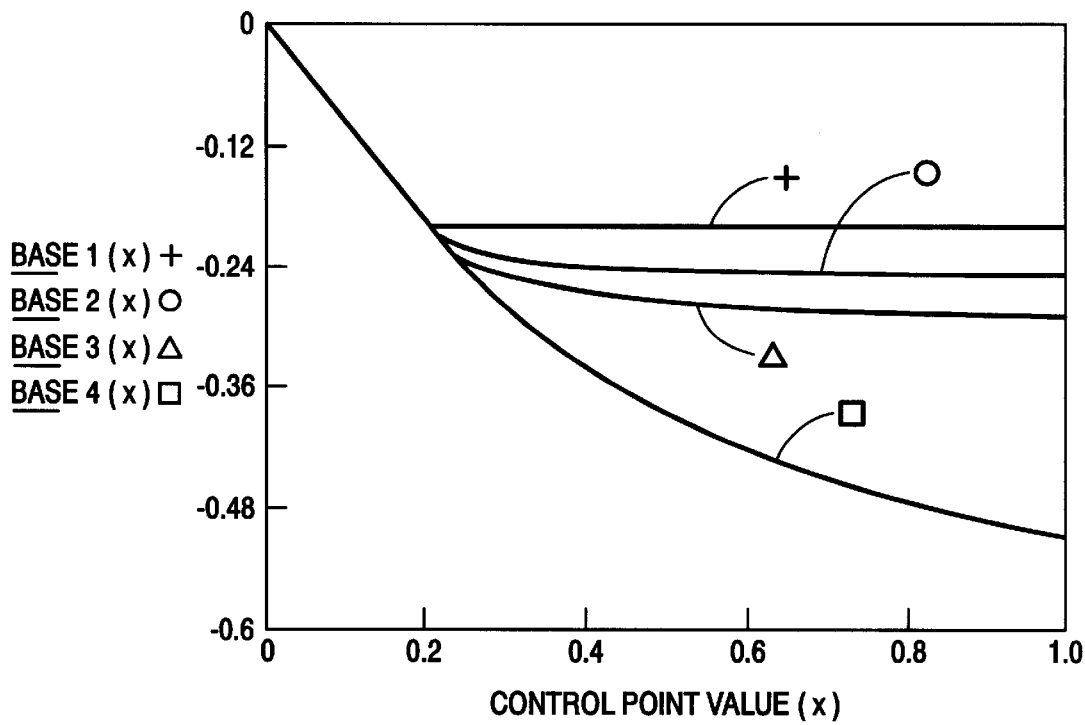
FIG. 8C BASE CHANGE ABSOLUTE
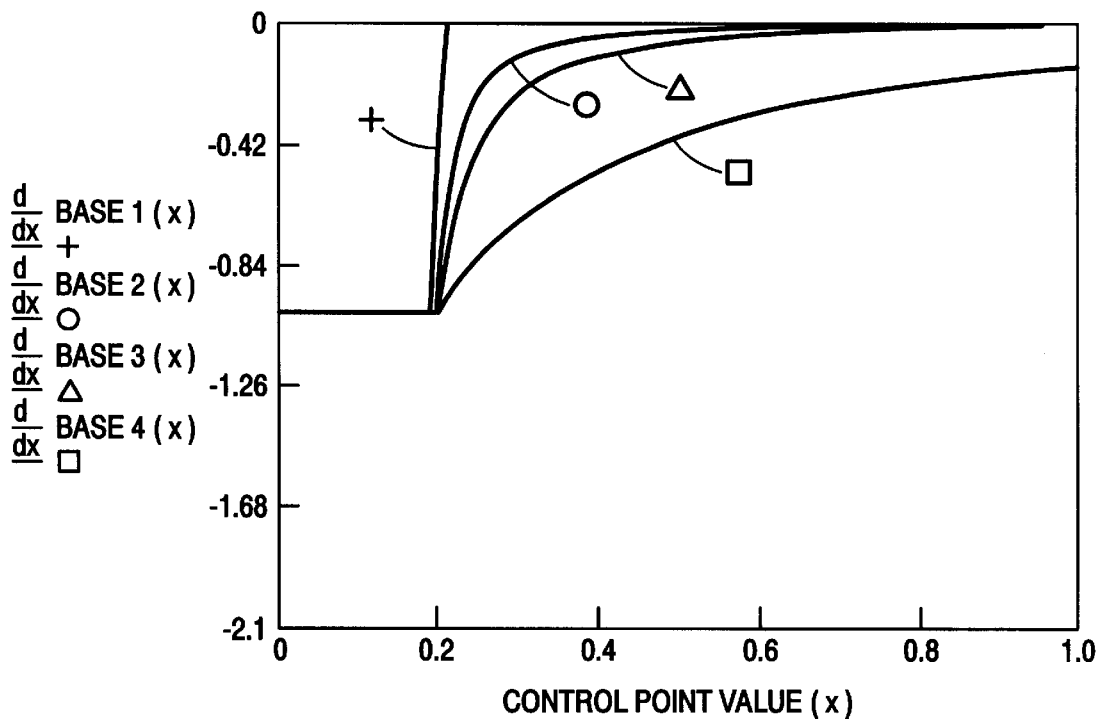
FIG. 8D BASE CHANGE SLOPE

PLANNING METHOD AND APPARATUS FOR RADIATION DOSIMETRY

RELATED APPLICATIONS

This application claims the benefit of U.S. Provisional Application No. 60/087,049, filed May 27, 1998.

BACKGROUND OF THE INVENTION

1. Field of the Invention

The invention relates to a method and apparatus for conformal radiation therapy of tumors with a radiation beam having a pre-determined, constant beam intensity.

2. Description of the Prior Art

Modern day radiation therapy of tumors has two goals: eradication of the tumor and avoidance of damage to healthy tissue and organs present near the tumor. It is known that a vast majority of tumors can be eradicated completely if a sufficient radiation dose is delivered to the tumor volume; however, complications may result from use of the necessary effective radiation dose, due to damage to healthy tissue which surrounds the tumor, or to other healthy body organs located close to the tumor. The goal of conformal radiation therapy is to confine the delivered radiation dose to only the tumor volume defined by the outer surfaces of the tumor, while minimizing the dose of radiation to surrounding healthy tissue or adjacent healthy organs.

Conformal radiation therapy has been traditionally approached through a range of techniques, and typically uses a linear accelerator ("LINAC") as the source of the radiation beam used to treat the tumor. The linear accelerator typically has a radiation beam source which is rotated about the patient and directs the radiation beam toward the tumor to be treated. The beam intensity of the radiation beam is a predetermined, constant beam intensity. Multileaf collimators, which have multiple leaf, or finger, projections which can be moved individually into and out of the path of the radiation beam, can be programmed to follow the spatial contour of the tumor as seen by the radiation beam as it passes through the tumor, or the "beam's eye view" of the tumor during the rotation of the radiation beam source, which is mounted on a rotatable gantry of the linear accelerator. The multiple leaves of the multileaf collimator form an outline of the tumor shape as presented by the tumor volume in the direction of the path of travel of the radiation beam, and thus block the transmission of radiation to tissue disposed outside the tumor's spatial outline as presented to the radiation beam, dependent upon the beam's particular radial orientation with respect to the tumor volume.

Another approach to conformal radiation therapy involves the use of independently controlled collimator jaws which can scan a slit field across a stationary patient at the same time that a separate set of collimator jaws follows the target volume as the gantry of the linear accelerator rotates. An additional approach has been the use of attachments for LINACs which allow a slit to be scanned across the patient, the intensity of the radiation beam in the entire slit being modified as the slit is being scanned.

A further approach for conformal radiation therapy treatment has been the use of a narrow pencil beam of high energy photons, whose energy can be varied, and the beam is scanned over the tumor target volume so as to deliver the best possible radiation dose distribution in each orientation of the gantry upon which the photon beam source is mounted.

A major problem associated with such prior art methods of conformal radiation therapy are that if the tumor volume has concave borders, or surfaces, varying the spatial configuration, or contour, of the radiation beam, is only successful part of the time. In particular, when the convolutions, or outer surfaces, of a tumor are re-entrant, or concave, in a plane parallel to the path of the radiation treatment beam, healthy tissue or organs may be disposed within the concavities formed by the outer tumor concave surfaces, as well as the fact that the thickness of the tumor varies along the path of the radiation beam.

In order to be able to treat tumors having concave borders, it is necessary to vary the intensity of the radiation beam across the surface of the tumor, as well as vary the outer configuration of the beam to conform to the shape of the tumor presented to the radiation beam. The beam intensity of each radiation beam segment should be able to be modulated to have a beam intensity related to the thickness of the portion of the tumor through which the radiation beam passes. For example, where the radiation beam is to pass through a thick section of a tumor, the beam intensity should be higher than when the radiation beam passes through a thin section of the tumor.

Dedicated scanning beam therapy machines have been developed wherein beam intensity modulation can be accomplished through the use of a scanning pencil beam of high energy photons. The beam intensity of this device is modulated by increasing the power of its electron gun generating the beam. The power increase is directed under computer control, as the gun is steered around the tumor by moving the gantry upon which it is mounted and the table upon which the patient lies. The effect is one of progressively "painting" the target with the thickness, or intensity, of the paint, or radiation beam intensity, being varied by the amount of paint on the brush, or how much power is applied to the electron gun, as the electron gun moves over the tumor. Such dedicated scanning beam therapy machines, which utilize direct beam energy modulation, are expensive and quite time consuming in their use and operation, and are believed to have associated with them a significant patient liability due to concerns over the computer control of the treatment beam itself.

Other methods and apparatus for conformal radiation therapy have been developed that spatially modulate the beam intensity of a radiation beam across a volume of tissue in accordance with the thickness of the tumor in the volume of tissue by utilizing a plurality of radiation beam segments. Such methods and apparatus utilize attenuating leaves, or shutters, in a rack positioned within the radiation beam before the beam enters the patient. The tumor is exposed to radiation in slices, each slice being selectively segmented by the shutters. However, a minor disadvantage of that method and apparatus results from the fact that only two slices of tissue volume may be treated with one rotation of the gantry of the linear accelerator. Although the slices may be of arbitrary thickness, greater resolution is accomplished by selecting slices for treatment that are as thin as possible. As the thickness of the treatment slices decreases, the time it takes to treat the patient increases because more treatment slices are required in order to treat the entire tumor volume.

A new method and apparatus for conformal radiation therapy, for use with a radiation beam having a predetermined, constant beam intensity for treatment of a tumor has been proposed in co-pending patent application Ser. No. 08/634,785 to Mark P. Carol, filed Apr. 19, 1996, which includes a radiation beam source for producing a radiation beam having a predetermined, constant beam intensity; at least a 3×3 checkerboard array having alternating radiolucent and radiopaque compartments, for separating the radiation treatment beam into an array of a plurality of beam segments; and means for independently modulating the beam intensity of the radiation beam segments to spatially modulate the beam intensity of the radiation treatment beam across the tumor.

The foregoing methods and apparatus are designed to minimize the portion of the structures being exposed to radiation. However, because exposure to surrounding structures cannot be completely prevented, treatment plans are desired that are optimized to eradicate the tumor volume while minimizing the amounts of radiation delivered to the surrounding structures. Existing methods and apparatus for optimizing treatment plans use a computer to rate possible plans based on score functions which simulate a physician's assessment of a treatment plan. However, existing methods and apparatus have proven to be insufficient.

Existing methods and apparatus utilize a computational method of establishing optimized treatment plans based on an objective cost function that attributes costs of radiation of various portions of both the tumor and surrounding tissues, or structures. One such computational method is known in the art as simulated annealing. Existing simulated annealing methods utilize cost functions that consider the costs of under-exposure of tumor volumes relative to over-exposure of surrounding structures. However, the cost functions used in existing methods do not account for the structure volumes as a whole, relying merely on costs related to discrete points within the structure, and further do not account for the relative importance of varying surrounding structure types. For example, certain structure types are redundant in their function and substantial portions of the structure volume can be completely eradicated while retaining their function. Other structure types lose their function if any of the structure is completely eradicated. Therefore, the more sensitive structure volumes can receive a measured dose of radiation so long as no portion of the structure is subjected to a lethal dose.

Existing cost functions utilized in the optimization of treatment plans do not account for such varying costs associated with the different types of structures. After the treatment plan is optimized, the physician currently must evaluate each computed treatment plan for compliance with the desired treatment objective. If the computed treatment plan does not successfully meet the treatment objectives, the optimization process is repeated until a treatment plan can be computed that meets the physician's treatment objectives for both the tumor volume and the surrounding structures. Further, existing methods and apparatus do not allow the physician to utilize the familiar Cumulative Dose Volume Histogram ("CDVH") curves in establishing the desired dose distributions.

Accordingly, prior to the development of the present invention, there has been no method or apparatus for conformal radiation therapy, for use with a radiation beam having a predetermined, constant beam intensity for treatment of a tumor which: is simple and economical to use; that has what is believed to be a high safety factor for patient safety; computes an optimal treatment plan to meet conflicting, pre-determined, treatment objectives of a physician, accounting for objectives in both the target tumor volume and multiple structure types; and utilizes CDVH curves in establishing the desired dose distributions for each target tumor volume and tissue and structure types using a cost function.

Therefore, the art has sought a method and apparatus for conformal radiation therapy, for use with a radiation beam having a predetermined, constant beam intensity for treatment of a tumor which: is simple and economical to use; that has what is believed to be a high safety factor for patient safety; which computes an optimal treatment plan to meet conflicting, pre-determined, treatment objectives of a physician, accounting for objectives in both the target tumor volume and multiple structure types; and which utilizes CDVH curves in establishing the desired dose distributions for each target tumor volume and tissue and structure types.

SUMMARY OF INVENTION

In accordance with the invention, the foregoing advantages have been achieved through the present apparatus.

In accordance with another aspect of the invention, the foregoing advantages have also been achieved through the present method The planning method and apparatus for radiation dosimetry, when compared with previously proposed prior art methods and apparatus, have the advantages of: being simple and economical to use; having what is believed to be a high safety factor for patient safety; computing an optimal treatment plan to meet conflicting, pre-determined, treatment objectives of a physician, accounting for objectives in both the target tumor volume and multiple tissue structure types, and utilizing CDVH curves in establishing the desired dose distributions for each target tumor volume and tissue and structure types.

BRIEF DESCRIPTION OF THE DRAWINGS

In the drawings:

FIG. 7 is a sequence of graphs, showing the effect of various influence function parameter profiles utilized a preferred embodiment of the influence function of the present invention.

While the invention will be described in connection with the preferred embodiment, it will be understood that it is not intended to limit the invention to that embodiment. On the contrary, it is intended to cover all alternatives, modifications, and equivalents, as may be included within the spirit and scope of the invention as to be defined by claims to be filed in a non-provisional application.

DETAILED DESCRIPTION OF THE INVENTION

Simulated annealing radiotherapy planning ("SARP") methods are well known in the art to compute optimized radiation beam arrangements to meet objective parameters of a physician with regard to conflicting treatment objectives of a tumor volume and its surrounding structures. Existing SARP methods utilize systematic algorithms to calculate a proposed, optimized beam arrangement. Modern LINACs radiate a tumor site by making multiple passes along varying arcs approaching the target volume along different entrance paths, each arc being directed toward a point central to a target volume, commonly referred to as an epicenter of the treatment volume. Each pass of the treatment beam will radiate the portions of the tumor and surrounding structures passing within that arc. By utilizing such multiple beam passes, certain portions of the treatment field are irradiated by only some of the beam arcs while other portions of the treatment field are irradiated by each beam arc, thereby causing the highest dose concentration to occur at the epicenter.

Figure 6B:
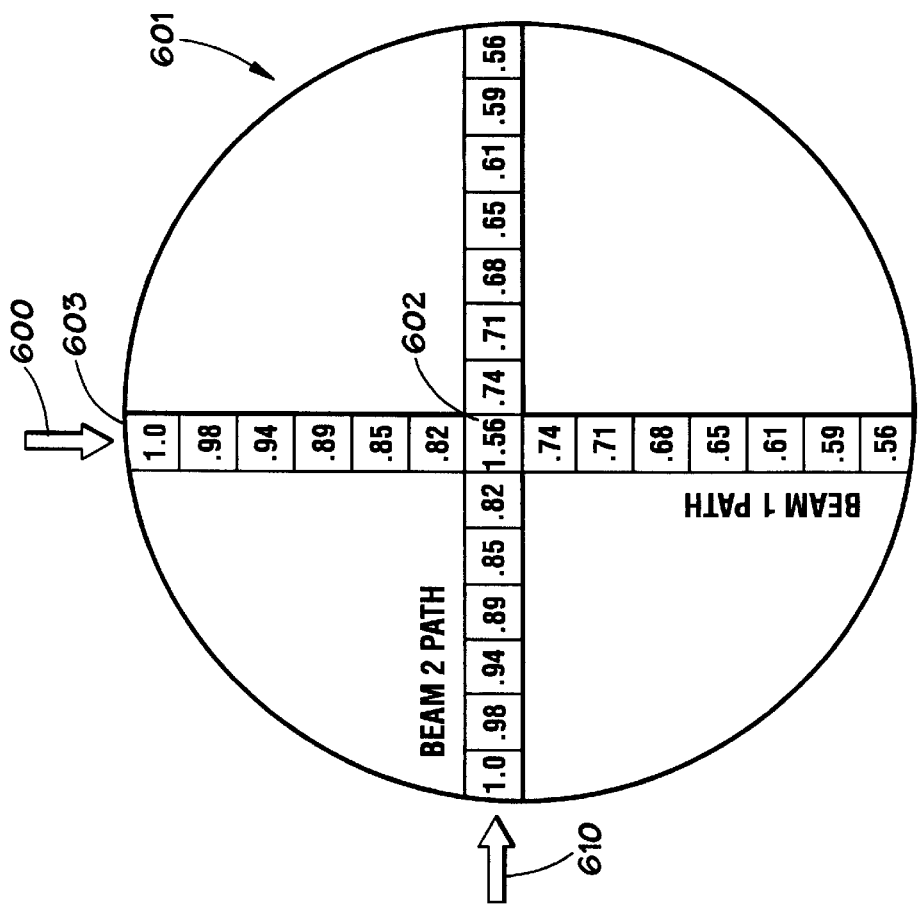
FIG. 6B is a dose treatment, showing the dose relationship of two beams passing through a treatment field.
Figure 6A:
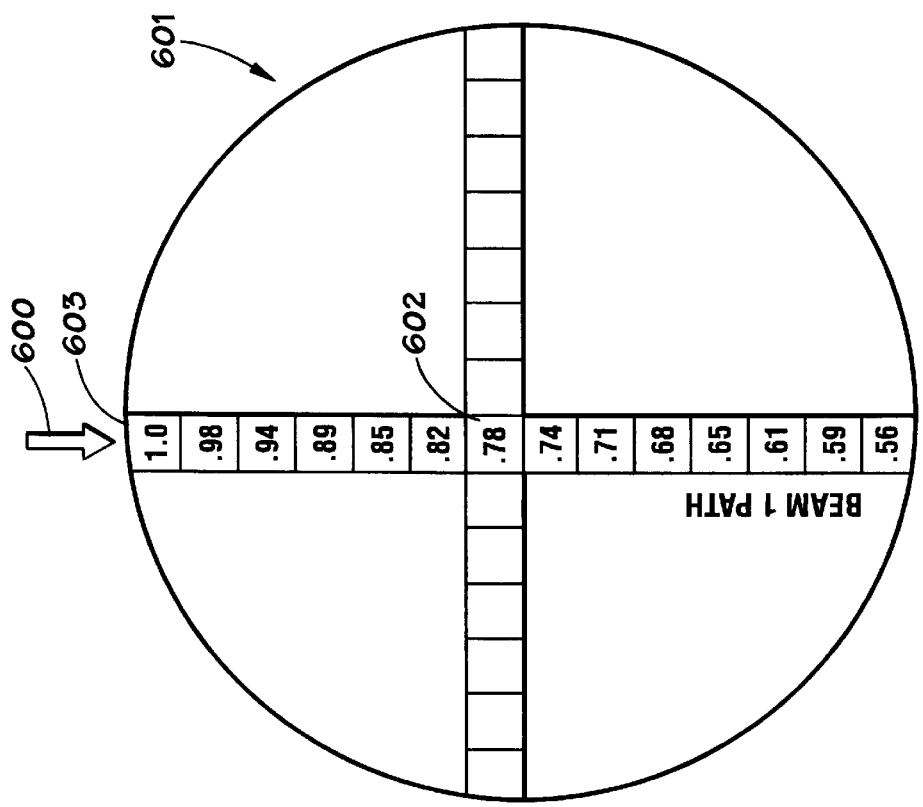
FIG. 6A is a dose treatment, showing the dose relationship of a single treatment beam passing through a treatment field.

Referring to FIGS. 6A and 6B, by way of example, FIG. 6A shows a dose relationship for the central ray of a single beam directed toward a treatment field from the direction indicated by arrow 600. The three-dimensional treatment field is shown projected on the two-dimensional grid 601. In this example, if a single beam is used, the beam weight, or intensity, at the epicenter 602 would be 78% of the dose at the entrance point 603. If a second beam of equal intensity were directed toward the treatment field from the direction indicated by arrow 610 (FIG. 6B) and placed so that the two beams intersected only at the epicenter 602, the dose at the epicenter 602 would be two times 78%, or 156% of the dose from each respective treatment beam. The cumulative effect of multiple beams passing through the treatment field from the different entrance paths 600, 610 thereby creates a concentration of dose to occur at the epicenter 602.

The optimal beam arrangement is arrived at by computationally increasing the proposed beam weight iteratively, incorporating cost functions to ensure that an iterative change in the beam weight would not result in an unacceptable exposure to the volumes of tissue or other structures being subjected to the proposed dose. At each iteration, the dose distribution resulting from the proposed beam selection is compared to a prescribed, or desired, dose for the tumor volume and surrounding tissue structures. If the increase or decrease in beam weights would lead to a greater correspondence to the desired prescription, the change is accepted. Ultimately, the SARP method will produce an optimized treatment plan, based on the treatment objectives as expressed by the cost function incorporated in the SARP algorithm.

Figure 1:
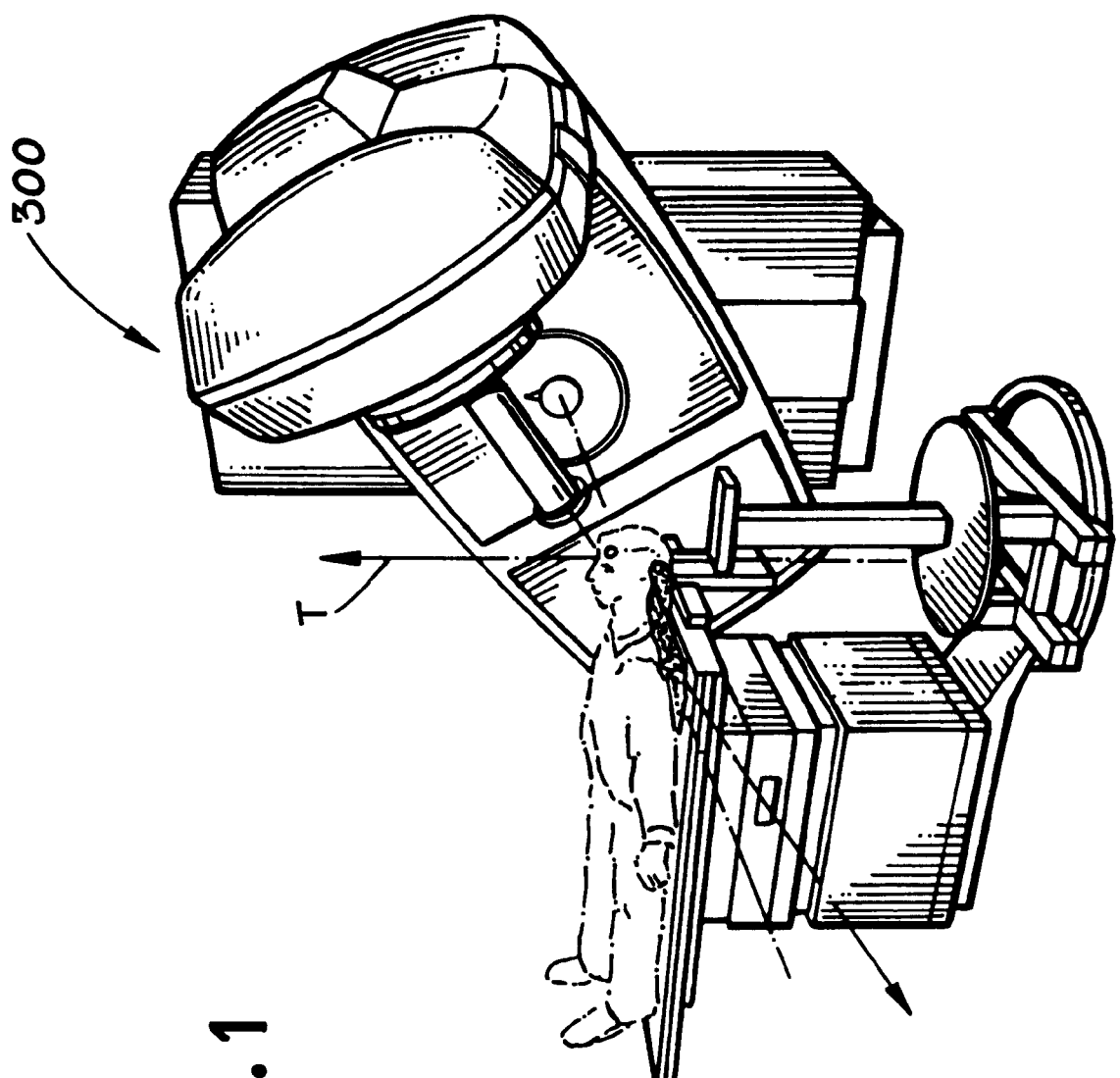
FIG. 1 is a perspective view of a conventional linear accelerator, including a rotatable couch, collimator and gantry.

The system of the present invention includes an improved optimized treatment planning system, which accounts for multiple treatment parameters for both a target and multiple surrounding structure types. The system includes a modified cost function, which allows a physician to use conventional cumulative dose volume histographs ("CDVH's") to establish a desired prescription of dosage to both the target volume, or target, and each involved structure volume, or structure, which will then be used as input for the system for determining the proposed dose distribution for delivery to a patient. The optimization method may be carried out using conventional equipment, including a conventional linear accelerator ("LINAC") 300, as shown in FIG. 1, having a rotatable gantry, a conventional computer or set of computers, and plan optimization software, which utilizes the optimization method of the present invention.

Figure 2:
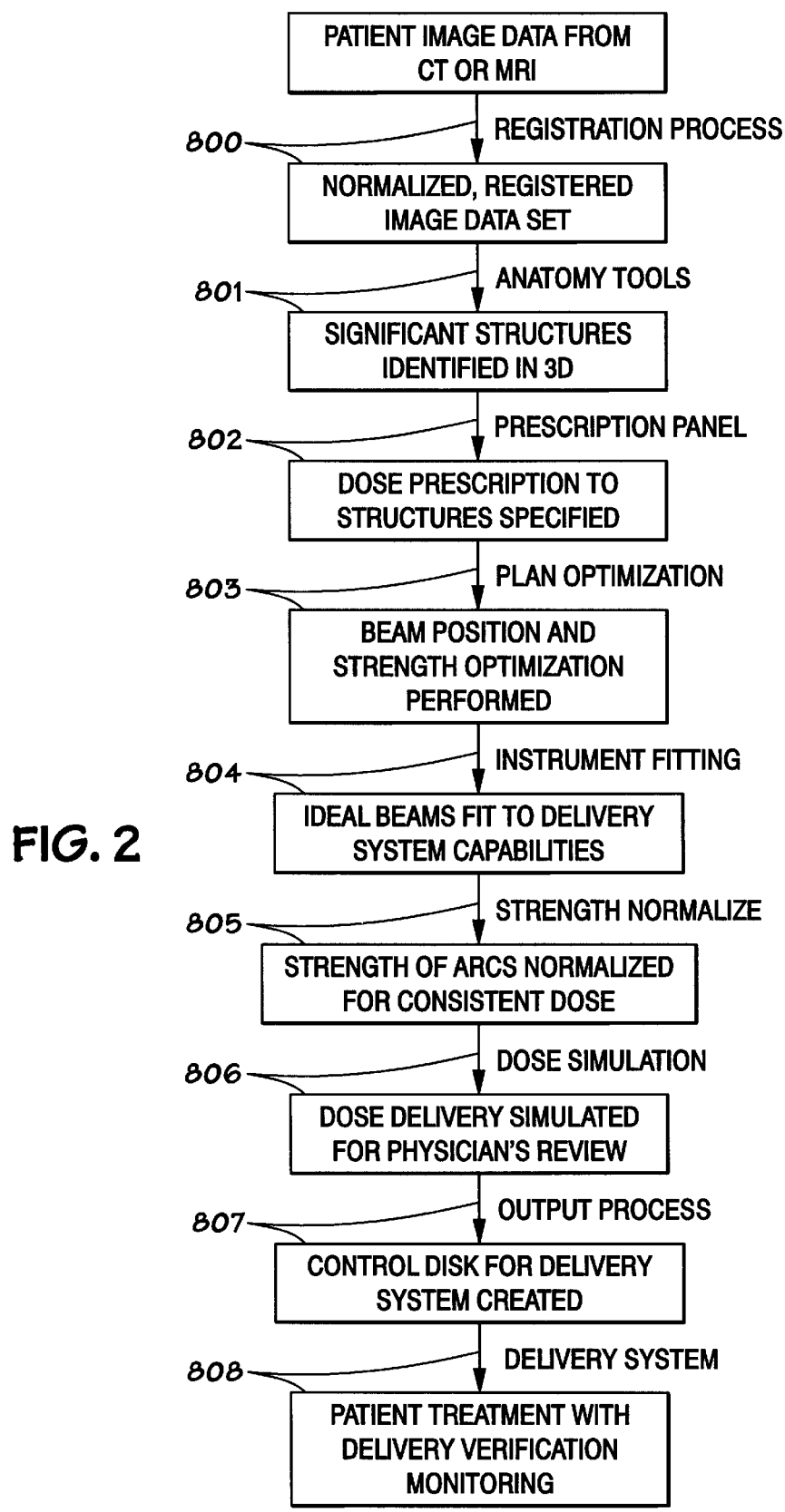
FIG. 2 is a flow diagram of a radiation planning system for controlling the operation of the apparatus of the present invention.

FIG. 2 shows a procedure for creating a treatment plan utilizing the system of the present invention. The first step of the method is generally referred to as the Registration Process step 800. This is the process step of aligning a set of conventional axial slice images of the portion of the patient to be treated by the conformal radiation therapy of the present invention. These images are first obtained by conventional computerized tomographic ("CT") scanning or magnetic resonance imaging ("MRI") techniques which produce an image representing a "slice" of tissue displayed with anatomical accuracy. The series of "slices," which constitute the complete CT or MRI study, represents a three-dimensional picture of a particular portion of the patient, to allow visualization as a valid three-dimensional data set. The resulting data is achieved by sampling the input data, determining common marks of known geometry, and warping the data to be correctly aligned. Resulting resolution is set so that it is geometrically correct based on the known patient fixation device utilized; and if images have been scanned from film, gray scale image normalization is done based on reference graybars including in the images. Conventional two-dimensional image warping techniques are utilized, with super sampling and filtering as required for resolution adjustment. Image slice spacing is entered by the operator of the planning system and verified by the known patient fixation device geometry.

The next step of the system is generally referred to as the Anatomy Tools step 801. The physician identifies the three-dimensional volume of the structure significant to radiation planning in a conventional manner, whereby the physician identifies anatomical structures on an image slice-by-slice basis.

The Prescription Panel step 802 allows the physician to input into the planning system the desired goal of the radiation therapy treatment, which is utilized in the plan optimization step 803.

Figure 3:
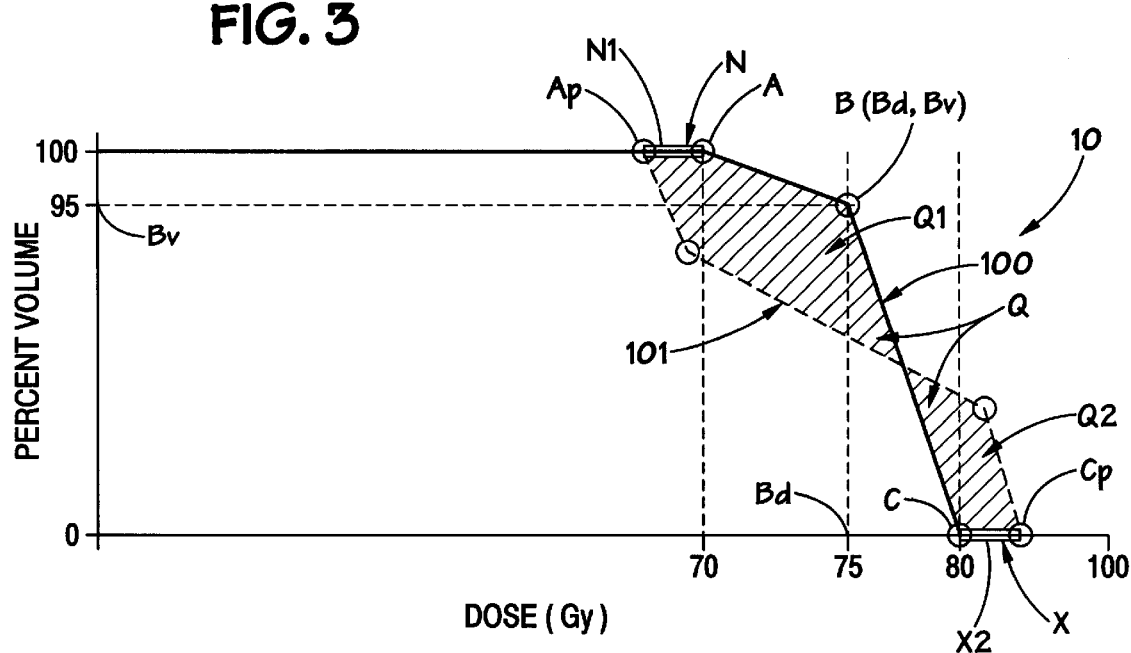
FIG. 3 is a composite target CDVH curve used in the system of the present invention, showing a proposed target CDVH curve and a desired target CDVH curve.
Figure 4:
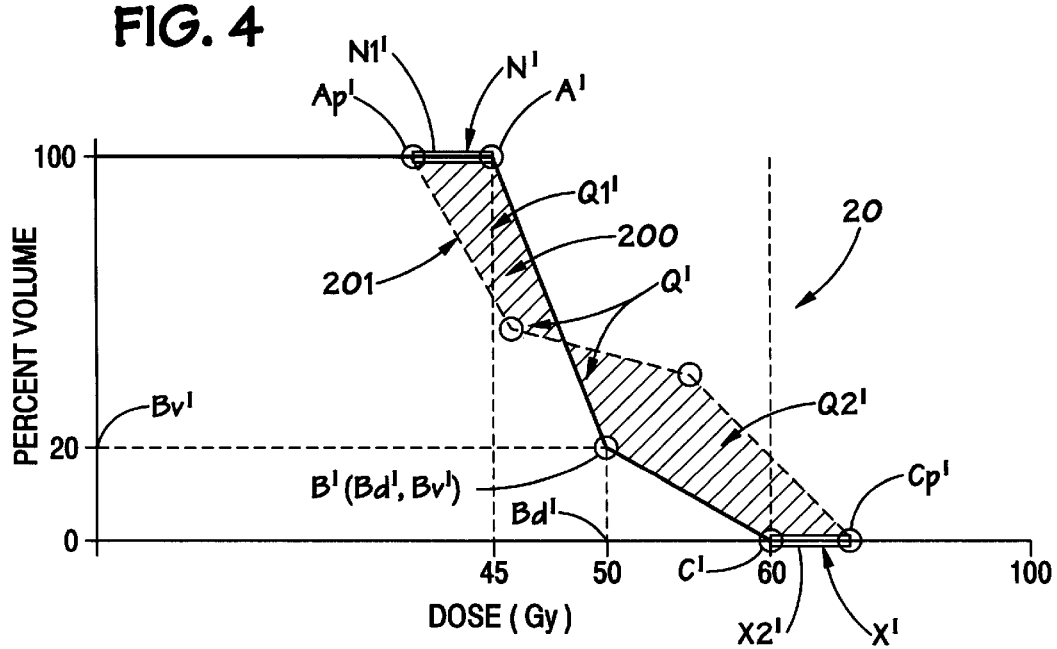
FIG. 4 is a composite structure CDVH curve used in the system of the present invention, showing a proposed structure CDVH curve and a desired structure CDVH curve.

FIGS. 3 and 4 show conventional desired target and structure CDVH curves 100, 200, respectively, which are typically used by a physician in reviewing the effect a given dose distribution will have on a target or structure before that dose distribution is applied to the patient. Physicians and those skilled in the art of radiation dosimetry are familiar with desired CDVH curves 100, 200; however, they are typically used to analyze a dose distribution after a treatment plan has been optimized. In contrast, the familiar desired CDVH curves 100, 200 are used by a physician using the system of the present invention not only in the Output Process step 807 (FIG. 2), but also prior to the Plan Optimization step 803 (FIG. 2), discussed hereinafter in detail, to establish partial volume data representing dosage limits and other desired parameters, as hereinafter discussed in detail, for each target and structure to establish the input parameters for the cost function of the present invention, which may be entered in the Prescription Panel step 802 (FIG. 2) of the present invention.

Figure 5:
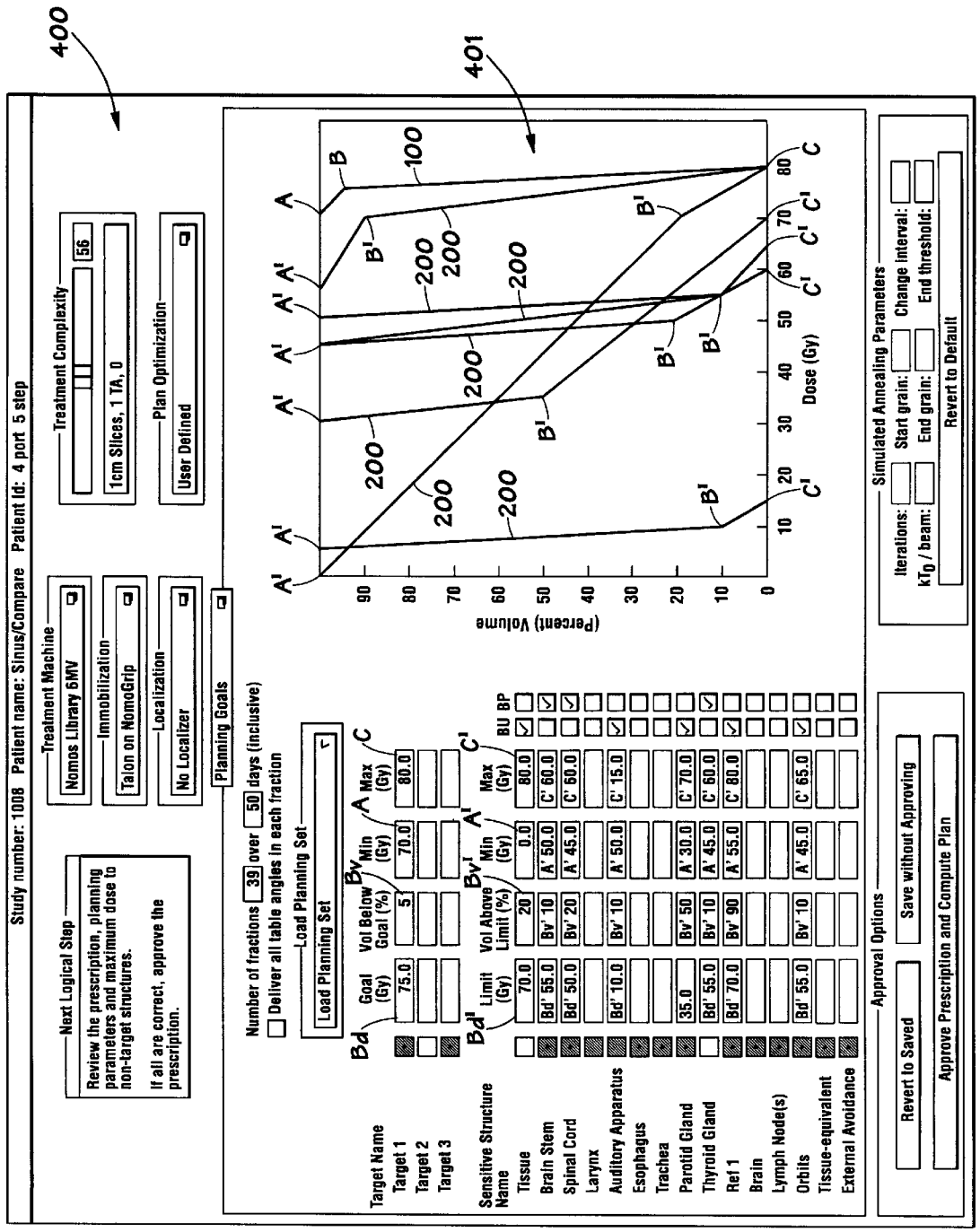
FIG. 5 is a prescription panel of the system of the present invention.

The desired CDVH curves 100, 200 utilized in the system of the present invention are created from partial volume data for each target and structure of a given patient. In the system of the present invention, partial volume data are entered by the user during the Prescription Panel step 802 (FIG. 2). FIG. 5 shows an embodiment of a prescription panel 400 used to input the partial volume data into the planning system of the present invention. The partial volume data generally describes what percent of the volume of a tumor or structure can receive how much dose. With reference now to FIG. 3, the partial volume data for a target may include data corresponding to values represented as data points on a desired target CDVH curve 100. The target dosage goal value Bd is the desired dose to be achieved in the target volume; the target maximum dosage value C is the maximum dose to be received by any portion of the target; the target minimum dosage value A is the minimum dose to be received by any portion of the target volume that will be underdosed; and the portion of the target volume which should have a dose greater than the goal may be represented by target percent over goal value Bv. The target dosage goal value Bd and target percent over goal value Bv comprises the co-ordinates of the data point B.

An illustrative desired target CDVH curve 100 is shown in FIG. 3. By way of example, a physician may determine that a given target volume must receive less than 80 Gy. Therefore, the target maximum dose value C would be 80 Gy, whereby no portion of the target volume could receive a cumulative dose greater than 80 Gy. Next, the physician may determine that the desired cumulative dose to the target volume should be 75 Gy and, that only five (5%) percent of the target volume should receive a cumulative dose less than 75 Gy. Therefore, ninety-five (95%) percent of the target volume should receive a cumulative dose greater than 75 Gy. Accordingly, the target dosage goal Bd would be 75 Gy and the target percent over goal value Bv would be ninety-five (95%) percent. Finally, the physician may determine that the entire target should receive a minimum dosage value of 70 Gy. Therefore, the target minimum dosage value A would be 70 Gy. The desired target CDVH curve 100 created when plotting these values as a conventional CDVH curve is shown in FIG. 3. After the physician has input the desired target goals into the system according to the Prescription Panel step 802 (FIG. 2), the system of the present invention may display the corresponding desired target CDVH curve 100 for review by the physician. Alternatively, the physician may be able to draw the desired target CDVH curve 100 graphically using a mouse or other pointing device and the system would then present the numeric values representing the target goals corresponding to the desired target CDVH curve 100.

Referring now to FIG. 4, an illustrative desired structure CDVH 200 is shown. By way of example, the partial volume data for a structure may include data corresponding to values represented as data points on a desired structure CDVH curve 200. The structure dosage limit value Bd' is the desired dosage limit not to be exceeded in the volume of a sensitive structure; the structure maximum dosage value C' is the maximum dose to be received by any portion of the structure; the structure minimum dosage value A' is the dose below which there is no appreciable benefit gained by reducing the exposure to the structure; and the portion of the structure volume which can have a dose greater than the goal dosage may be represented by structure percent over limit value Bv'. The structure dosage limit value Bd' and structure percent over limit value Bv' comprise the coordinates of the data point B'.

An illustrative desired structure CDVH curve 200 is shown in FIG. 4. By way of example, a physician may determine that a given structure volume must receive less than 60 Gy. Therefore, the structure maximum dose value C' would be 60 Gy, whereby no portion of the structure volume can receive a cumulative dose greater than 60 Gy. Next, the physician may determine that the desired cumulative dose limit to the structure volume should be 50 Gy and that only twenty (20%) percent of the structure volume should receive more than this cumulative dose. Therefore, eighty (80%) percent of the structure volume should receive a cumulative dose less than 50 Gy. Accordingly, the structure dosage limit Bd' would be 50 Gy and the structure percent over goal value Bv' would be twenty (20%) percent. Finally, the physician may determine that there is no appreciable benefit gained by reducing the exposure to the structure below 45 Gy. Therefore, the structure minimum dosage value A' would be 45 Gy. The desired structure CDVH curve 200 created when plotting these values as a conventional desired CDVH curve is shown in FIG. 4. After the physician has input the desired structure goals into the system according to the Prescription Panel step 802 (FIG. 2), the system of the present invention may display the corresponding target and structure desired CDVH curves 100, 200 for review by the physician. Alternatively, the physician may be able to draw the desired target and structure CDVH curves 100, 200 graphically using a mouse or other pointing device and the system would then present the numeric values representing the target goals corresponding to the desired CDVH curves 100, 200. In any event, the resulting desired CDVH curves for both the target and the structures can be compared to ensure that the structure curves fit within the bounds of the target curves. This can be accomplished by overlaying the graphs manually or, in a preferred embodiment, by simultaneously displaying the graphs alongside the numerical representations of the partial volume data, as shown in FIG. 5.

FIG. 5 shows an embodiment of a prescription panel 400 used in the Prescription Panel step 802 (FIG. 2) of the present invention in which numerical values are entered for the partial volume data for each target and structure. The corresponding desired target and structure CDVH curves 100, 200 are displayed in a graphical window 401.

In the Plan Optimization step 803, the radiation plan optimization is a specific case of an inverse problem, where the goal is to determine the best way to achieve the dose prescription. A SARP technique is utilized to do this optimization by dividing the radiation delivery into a large number of small beams, each of which hit the target. The annealing cooling schedule utilized, fits into the class of FSA (Fast Simulated Annealing) techniques. Except for the foregoing detailed description of the cost function utilized in the present system, the details of the foregoing simulated annealing techniques are known in the art and are described in such publications as "Optimization of Conformal Radiotherapy Dose Distributions by Simulated Annealing," S. Webb, Physics and Medical Biology, Vol. 34, PP. 1349–1370 (1989); and "Optimization of Conformal Radiotherapy Dose Distributions by Simulated Annealing: 2. Inclusion of Scatter in the 2d Technique," S. Webb, Physics and Medical Biology, vol.36, pp. 1227–1237, (1991), which publications are incorporated herein by reference. A suitable computer is utilized in performing the Plan Optimization step 802 (FIG. 2), as well as the other steps of the radiation planning system. For illustration purposes only, a programmable 150 Mhz pentium computer with four symmetric multiprocessors, running the Sun Solaris operating system, and having 256 megabytes RAM could be utilized in performing the Plan Optimization step 802 (FIG. 2).

Referring again to FIGS. 3 and 4, proposed CDVH curves 101, 201, which reflect the effect of a prescription proposed by the system during a given iteration of the Plan Optimization step 803 (FIG. 2), are shown overlayed on respective desired target and structure CDVH curves 100, 200. The resulting composite CDVH curves 10, 20 include desired target or structure CDVH curves 100, 200 and proposed target or structure CDVH curves 101, 201. Certain control points or regions N, N', Q, Q', X, and X' of the composite CDVH curves 10, 20 may be identified as being more important for a particular type of target or structure. Relative parameters, as described in detail hereinafter, are then assigned by the computer after experimental generation by the system developer that will achieve the desired objective of each type of target or structure when applied by a particular cost function of the present invention, as further described below.

In a preferred embodiment, composite target volume CDVH curve 10 (FIG. 3) comprises 3 control points or regions N, Q, and X. Each of those control points or regions N, Q, X have two values associated therewith, as follows. Values for N include N1, representing the total linear distance on composite target CDVH curve 10 between the desired minimum dose A on desired target CDVH curve 100 and proposed minimum dose Ap on proposed target CDVH curve 101 when the proposed minimum dose A on the proposed target CDVH curve 101 is to the left of the desired minimum dose A on the desired target CDVH curve 100, and N2 (not shown), representing the total linear distance on composite target CDVH curve 10 between the desired minimum dose A on desired target CDVH curve 100 and proposed minimum dose $A_p$ on proposed target CDVH curve 101 when the proposed minimum dose $A_p$ on the proposed target CDVH curve 101 is to the right of the desired minimum dose A on the desired target CDVH curve 100. For a given iteration, either N1 or N2 will necessarily be equal to zero because the proposed minimum dose $A_p$ will be either less than or greater than the desired minimum dose A and not both. Similarly, values for Q include $Q_1$, representing the total area between proposed CDVH curve 101 and desired target CDVH curve 100 being below and to the left of the desired target CDVH curve 100, and Q2, representing the total area between the proposed target CDVH curve 101 and desired CDVH curve 100 being above and to the right of the desired target CDVH curve 100. Likewise, values for X include X1 (not shown), representing the total linear distance on composite target CDVH curve 10 between the proposed maximum dose $C_p$ on proposed target CDVH curve 101 and desired maximum dose C on desired target CDVH curve 100 when the proposed maximum dose $C_p$ on the proposed target CDVH curve 101 is to the left of the desired maximum dose C on the desired target CDVH curve 100, and X2, representing the total linear distance on composite target CDVH curve 10 between the proposed maximum dose $C_p$ on proposed target CDVH curve 101 and desired maximum dose C on desired target CDVH curve 100 when the proposed maximum dose C on the proposed target CDVH curve 101 is to the right of the desired maximum dose C on the desired target CDVH curve 100. For a given iteration, either X1 (not shown) or X2 will necessarily be equal to zero because the proposed maximum dose $C_p$ will be either less than or greater than the desired maximum dose C and not both.

Similarly, in a preferred embodiment, composite structure volume CDVH curve 20 (FIG. 4) comprises 3 control points or regions N', Q', and X'. Each of those control points or regions N', Q', X' have two values associated therewith, as follows. Values for N' include N1', representing the total linear distance on composite structure CDVH curve 20 between the desired minimum dose A' on desired structure CDVH curve 200 and proposed minimum dose $A_p'$ on proposed structure CDVH curve 201 when the proposed minimum dose $A_p'$ on the proposed structure CDVH curve 201 is to the left of the desired minimum dose A' on the desired structure CDVH curve 200, and N2' (not shown), representing the total linear distance on composite structure CDVH curve 20 between the desired minimum dose A' on desired structure CDVH curve 200 and proposed minimum dose $A_p'$ on proposed structure CDVH curve 201 when the proposed minimum dose $A_p'$ on the proposed structure CDVH curve 201 is to the right of the desired minimum dose A' on the desired structure CDVH curve 200. For a given iteration, either N1' or N2' (not shown) will necessarily be equal to zero because the proposed minimum dose $A_p'$ will be either less than or greater than the desired minimum dose A' and not both. Similarly, values for Q' include $Q1'$, representing the total area between proposed structure CDVH curve 201 and desired structure CDVH curve 200 being below and to the left of desired structure CDVH curve 200, and Q2', representing the total area between the proposed structure CDVH curve 201 and desired structure CDVH curve 200 being above and to the right of the desired structure CDVH curve 200. Likewise, values for X' include X1' (not shown), representing the total linear distance on composite structure CDVH curve 20 between the proposed maximum dose $C_p'$ on proposed structure CDVH curve 201 and desired maximum dose C' on the desired structure CDVH curve 200 when the proposed maximum dose $C_p'$ on the proposed structure CDVH curve 201 is to the left of the desired maximum dose C' on the desired structure CDVH curve 200, and X2', representing the total linear distance on composite structure CDVH curve 20 between the proposed maximum dose $C_p'$ on the proposed structure CDVH curve 201 and desired maximum dose C' or the desired structure CDVH curve 200 when the proposed maximum dose $C_p'$ on the proposed structure CDVH curve 201 is to the right of the desired maximum dose C' on the desired structure CDVH curve 200. For a given iteration, either X1' (not shown) or X2' will necessarily be equal to zero because the proposed maximum dose $C_p'$ will be either less than or greater than the desired maximum dose C' and not both.

The cost function is an analytical determination of whether, when any change is made to the strengths of the beams being used to treat the patient, the resultant dose distribution is closer to the result desired by the user. In the cost function of the present invention, each control point or control region value described above is used as an input variable to a parameterized influence function for each target or structure, as described hereinafter in detail. The resultant values from the influence function calculation for each control point or control region value of each target and structure are summed to produce a final cost of the proposed beam weights reflected by proposed CDVH curve 101, 201 during a given iteration of the Plan Optimization step 803 (FIG. 2).

In a particular embodiment, a particular influence, or cost, function could be expressed according to the following formula:

$$INF_1(x, scale, base, offset) = \begin{vmatrix} basex - offset^3 + scalex, \text{ if } x \geq offset \\ scalex, \text{ if } x < offset \end{vmatrix},$$

where x represents a given control point value for a given pair of proposed and desired CDVH curves; offset represents a predetermined value along an influence curve (representing the influence function as a function of the control point value x) where the influence curve turns from linear to exponential according to the above equation; scale represents a predetermined value which controls the influence function up to the point along the influence curve at which the value of x equals the offset value; and base represents a predetermined value which controls the influence function beyond the point along the influence curve at which the value of x equals the offset value. The above influence function $INF_1$ will be linear for values of x less than the offset value and will be cubic for values of x beyond the offset value.

In another embodiment, a particular influence, or cost, function could be expressed according to the following formula:

$$INF_2(x, scale, base, offset) = \left| \begin{array}{l} -scale\left[\dfrac{(x-offset)^2}{x-offset+base}\right] + scale(x), \text{ if } x \geq offset \\ scale(x), \text{ if } x < offset \end{array} \right.$$

where x represents a given control point value for a given pair of proposed and desired CDVH curves; offset represents a predetermined value along an influence curve (representing the influence function as a function of the control point value x) where the influence curve turns from linear to exponential according to the above equation; scale represents a predetermined value which controls the influence function up to the point along the influence curve at which the value of x equals the offset value; and base represents a predetermined value which controls the influence function beyond the point along the influence curve at which the value of x equals the offset value. Parameter values for scales, offset, and base are selected in the same manner as described in connection with $INF_1$. Like $INF_1$, $INF_2$ will be linear up to the offset value; however, after the offset the slope actually declines. This creates a plateau or region in which there is almost no influence driving the cost in either direction. This influence function is intended for use in regions where, after a certain goal is reached, there is little difference in staying at that goal or going beyond it. If it is used in a situation where going beyond the goal is not desirable, a control point value way out on the plateau will not be influenced much to move towards the lower value.

A value is calculated for each control point value N1, N2, Q1, Q2, X1, X2, N 1', N2', Q1', Q2', X1', and X2' of each CDVH curve of each target and structure according to the influence function $INF_1$ or $INF_2$. The total cost for the proposed dose represented by the proposed CDVH curve may then be obtained by summing each value of $INF_1$ or $INF_2$ for each control point value of each CDVH curve of each target and structure. As described in detail hereinafter, it should be noted that each target and structure will have a different influence profile, which specifies particular values for the influence parameters scale, base, and offset according to the relative sensitivity of that target or structure to the radiation beam being used. Those values are predetermined and assigned by the computer after experimental generation by the system developer to achieve the desired objective of each type of target or structure when applied by the cost function of the present invention; however, in a particular embodiment, the values could also be assigned by the user for a particular type of target or structure.

For each target and structure, a set of parameters scale, offset, and base form an influence profile for that target or structure. The values for scale, offset, and base are predetermined for a particular target or structure type. However, each scale, offset, and base parameter may have two values associated therewith that are used by the influence function depending on whether the relevant control point or control region A, Q, X, A', Q', X' on the composite CDVH curve 10, 20 resulting from the proposed dose and the desired dosage limits for that target or structure fall to the left of the desired target or structure CDVH curve 100, 200 or fall to the right of the desired target or structure CDVH curve 100, 200. For example, the influence function will utilize −scale, −offset, and −base values for the scale, offset, and base parameters when calculating the costs associated with the control points or regions represented by control point or region values N1, N1', Q1, Q1', X1, and X1'. Likewise, the influence function will utilize +scale, +offset, and +base values for the scale, offset, and base parameters when calculating the costs associated with the control points or regions represented by control point or region values N2, N2', Q2, Q2', X2, and X2'.

Thus, for each structure or target, 6 parameter values are assigned that collectively determine the relative importance of doing better or worse than the desired CDVH curve 100, 200. For instance, there may be structures where the dose tolerance limits are well understood and very well defined. If a plan meets these limits, function will be preserved; if the plan exceeds these limits, function will be lost and improving on them will impart no added benefit. Alternatively, the response of certain structures may not be well understood; exceeding maximum dose may not be a problem and improving on the minimum dose may not afford any benefit, but since the overall dose response curve of the structure is not known, slightly overdosing the whole organ may not cause much harm while reducing overall dose to the structure may be of benefit.

The values assigned to these +/−scale, +/−offset, and +/−base parameter values codify the system developer's knowledge of each type of target and structure and will determine how the optimizer resolves conflicts between structures and targets. As an example, a set of values could be created that strongly favors sparing sensitive structures over treating the entire target but does not make any attempt to improve on the desired structure CDVH curves 200. In order to achieve such a result, the +offset value for all of the costs for each structure would be set at "0", the +scale value would be set to a high value, and the +base value would be set to an extremely high value. This implies that it is very expensive to exceed, even to a small degree, the desired structure CDVH curve 200 for that structure. All − parameter values would be set at zero, implying that there is no benefit to improving on the desired structure CDVH curve 200 for that structure. For a target, each +parameter value would be set to zero, implying that there is no benefit to doing better than the desired target CDVH curve 200; the −offset value would be large; the −scale value would be low; and the −base value low, implying that there is a large amount of leeway given to underdosing the target. Effectively, all beam changes that improve the proposed target CDVH curve 201 but worsen the proposed structure CDVH curve 101 would be rejected. Any other beam changes would be accepted.

Alternatively, a set of values could be created that allows structure limits to be exceeded by a set amount if such excess allows better conformation to the desired target CDVH curve 100. By setting all structure +offsets to 10%, making all +scale values high and all +base values extremely high while at the same time setting all −target offset values to zero, all −scale values to a low value and all −base values low, the targets will be favored over the structures until the proposed structure CDVH curve 201 exceeds the desired structure CDVH curve 201 by 10%. If that point is reached, no further worsening of structure limits would be allowed. These tradeoffs can be fine tuned even further by assigning different values to the + and − parameter values for each of the three costs associated with a structure or target. For instance, by setting the +X offset for a structure high and the −N offset for a structure low, tolerance for exceeding maximum dose to a structure would be allowed if it improves minimum dose to a target. If, however, the +Q offset for the structure was set low, then this tradeoff would not occur if it worsened overall dose to the structure.

Accordingly, by assigning different influence parameters to different target or structure CDVH curves in the system, different results will be obtained by the user. Therefore, the influence parameters are incorporated into the software with an outcome in mind, and the system developer must understand what kind of results the assigned influence parameters will produce. The system developer should be able to choose the desired influence parameters without undue experimentation to achieve a desired outcome in the system by the user. For instance, in one implementation of the invention, sparing of sensitive structures is preferred over treating the entire target in order to avoid complications which can result from the delivery of radiation. Sparing of sensitive structures is accomplished by delivering a dose distribution whereby the proposed structure CDVH curve, or structure pseudo-curve is equivalent to or better than the desired structure CDVH curve. In order to achieve this result, influence parameters must be provided by the system developer so that if a beam change is made that improves the proposed target CDVH curve, or target pseudo-curves, but worsens the proposed structure CDVH curves, or structure pseudo-curves, the change will be rejected. The actual influence parameter values assigned are based upon clinical experience by one skilled in the art of inverse treatment planning system development. These influence parameter values can then be programmed into the system so they can be used repeatedly to produce a desired outcome.

The effect of influence function $INF_1$ on the cost associated with a particular control point or region based on the following illustrative influence profiles having various values for the scale, base, and offset parameters can be seen in FIG. 7:

x:=0,0.1 . . . ,1

| Influence Profile 1 | Influence Profile 2 |
|---|---|
| Scale1 (x): = Influence (x, 0, 4, 0.2) | Scale2 (x): = Influence (x, 0.5, 4, 0.2) |
| Base1 (x): = Influence (x, 1, 0, 0.2) | Base2 (x): = Influence (x, 1, 2, 0.2) |
| Offset1 (x): = Influence (x, 1, 4, 0.0) | Offset2 (x) : = Influence (x, 1, 4, 0.2) |
| Influence Profile 3 | Influence Profile 4 |
| Scale3 (x): = Influence (x, 1, 4, 0.2) | Scale4 (x): = Influence (x, 2, 4, 0.2) |
| Base3 (x): = Influence (x, 1, 4, 0.2) | Base4 (x): = Influence (x, 1, 8, 0.2) |
| Offset3 (x): = Influence (x, 1, 4, 0.4) | Offset4 (x): = Influence (x, 1, 4, 0.6) |

As can be seen in FIG. 7, $INF_1$'s first derivative always increases as the input gets more positive. This implies that the larger the value of a control point becomes, the more influenced it is to get smaller. The shape of the curve is linear up to the offset value, where it becomes cubic. This allows an "elbow" to be created, so that there is a region of little influence and then a region of very strong influence.

Figure 8E:
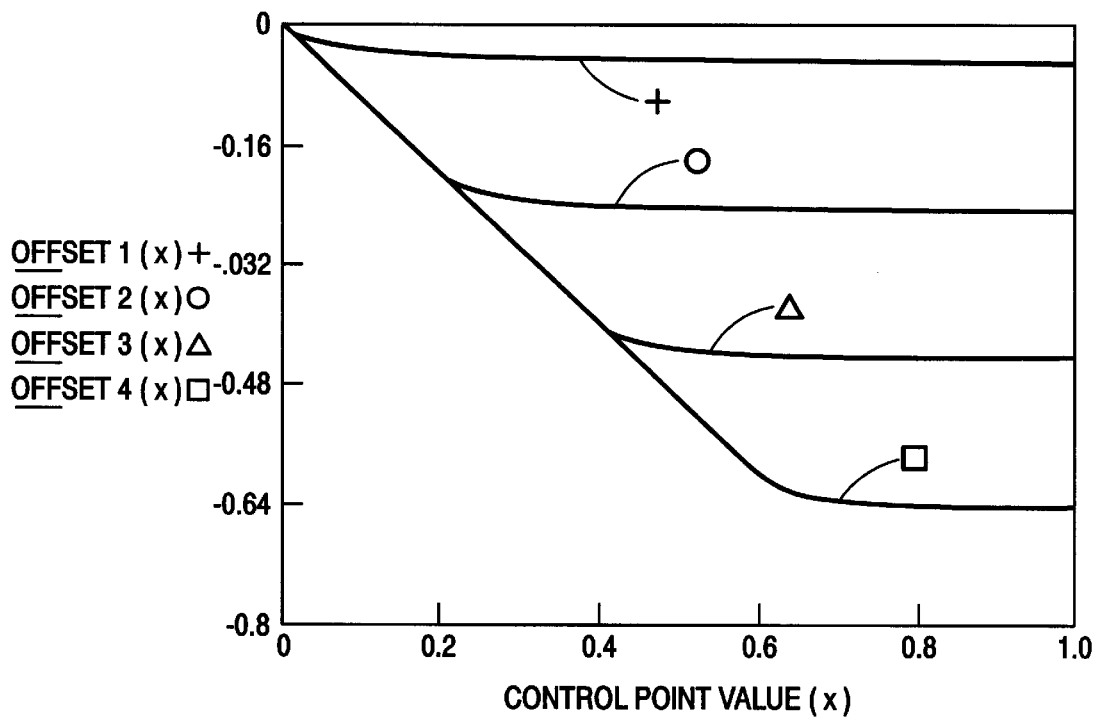
FIG. 8 a sequence of graphs, showing the effect of various influence function parameter profiles utilized by an alternative embodiment of the influence function of the present invention.
Figure 8F:
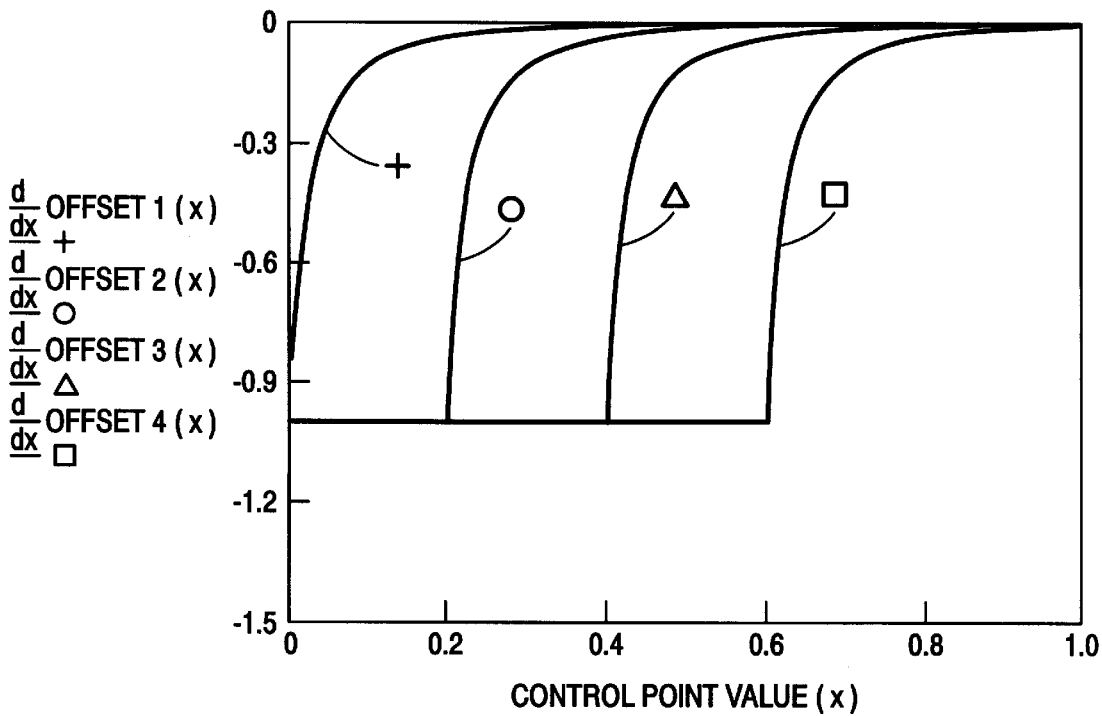

The effect of influence function $INF_2$ on the cost associated with a particular control point or region based on the following illustrative influence profiles having various values for the scale, base, and offset parameters can be seen in FIG. 8:

x:=0,0.01 . . . ,1

| Influence Profile 1 | Influence Profile 2 |
|---|---|
| Scale1 (x): = Influence (x, −2, 0.5, 0.2) | Scale2 (x): = Influence (x, −1, 0.5, 0.2) |
| Base1 (x): = Influence (x, −1, 0, 0.2) | Base2 (x): = Influence (x, −1, 0.05, 0.2) |
| Offset1 (x): = Influence (x, −1, 0.05, 0.0) | Offset2 (x): = Influence (x, −1, 0.05, 0.2) |
| Influence Profile 3 | Influence Profile 4 |
| Scale3 (x): = Influence (x, 0, 0.5, 0.2) | Scale4 (x): = Influence (x, 1, 0.5, 0.2) |
| Base3 (x): = Influence (x, −1, 0.1, 0.2) | Base4 (x): = Influence (x, −1, 0.5, 0.2) |
| Offset3 (x): = Influence (x, −1, 0.05, 0.4) | Offset4 (x): = Influence (x, −1, 0.05, 0.6) |

As can be seen in FIG. 8, $INF_2$ is linear up to the offset like $INF_1$; however, after the offset the slope actually declines. This creates a "plateau" or a region in which there is almost no influence driving the cost in either direction. This influence function is intended for use in regions where, after a certain goal is reached, there is little difference in staying at that goal or going beyond it. If it is used in a situation where going beyond the goal is not desirable, a control point value far out on the plateau will not be highly influenced to move towards the lower value.

Separate parameter profiles may be provided for each control point for each target, tissue, and structure type depending on how important the object (i.e., the target, tissue, or structure) may be to the physician. For example, for each such object, the user may select a checkbox, which can be checked for objects that are relatively important compared to the other objects, or unchecked for objects that are less important. In addition to the control points previously identified, a conformality control can also be provided to allow the physician or other user of the system to include the degree to which the proposed treatment plan conforms to the shape of the targets in the cost equation in order to minimize irradiation of normal tissue. The cost of conformality may be included in the calculation of the total cost of the proposed treatment plan and the conformality control will have a set of influence parameters to be used in the influence equations to be incorporated in the total cost by the system. Like the control points for the various objects, the conformality control may also be checked or unchecked depending on how important conformality is to the physician, or user, and separate paramaters may be provided depending on the checked state. In a particular embodiment, the system may also provide the user with a range of values to indicate the importance of each of the objects or the conformity control to the user. In such an embodiment, separate parameter profiles may be provided depending on the value of the user's selection within the range for each object or conformality control.

In a preferred embodiment, the following parameter values and influence functions could be used for the following target, structure, and tissue types to create a complete set of influence profiles to be used in the system:

|  |  | Control | Scale | Scale | Base | Base | Offset | Offset | IF | IF |
|---|---|---|---|---|---|---|---|---|---|---|
| Target | Q1 | 10 | 15 | 75 | 100 | 0.06 | 0.02 | $Inf_1$ | $Inf_1$ |
|  | Q2 | 10 | 10 | 10 | 50 | 0.05 | 0.02 | $Inf_1$ | $Inf_1$ |
|  | N1 | 45 | 50 | 90 | 100 | 0.06 | 0.03 | $Inf_1$ | $Inf_1$ |
|  | N2 | −1 | −10 | 0.0001 | 0.0001 | 0.2 | 0.2 | $Inf_2$ | $Inf_2$ |
|  | X1 | 0.1 | 0.1 | 0.0001 | 0.0001 | 0.2 | 0.2 | $Inf_2$ | $Inf_2$ |
|  | X2 | 5 | 5 | 200 | 200 | 0.15 | 0.1 | $Inf_1$ | $Inf_1$ |
| Tissue | Q1 | 0 | 0 | 0 | 0 | 0 | 0 | $Inf_1$ | $Inf_1$ |
|  | Q2 | 0 | 0 | 0 | 0 | 0 | 0 | $Inf_1$ | $Inf_1$ |
|  | N1 | 0 | 0 | 0 | 0 | 0 | 0 | $Inf_1$ | $Inf_1$ |
|  | N2 | 0 | 0 | 0 | 0 | 0 | 0 | $Inf_1$ | $Inf_1$ |
|  | X1 | 0 | 0 | 0 | 0 | 0 | 0 | $Inf_1$ | $Inf_1$ |
|  | X2 | 10 | 10 | 125 | 125 | 0 | 0 | Inf1 | Inf1 |
| BU | Q1 | −0.001 | 0.1 | 0 | 0.01 | 0.05 | 0.2 | $Inf_2$ | $Inf_2$ |
|  | Q2 | 7.5 | 15 | 125 | 125 | 0.1 | 0.05 | $Inf_1$ | $Inf_1$ |
|  | N1 | −0.1 | −0.05 | 0.0001 | 0.01 | 0.1 | 0.2 | $Inf_2$ | $Inf_2$ |
|  | N2 | 1 | 2 | 0 | 50 | 0.1 | 0.075 | $Inf_2$ | $Inf_1$ |
|  | X1 | −0.2 | −0.007 | 0 | 0.01 | 0.05 | 0.1 | $Inf_2$ | $Inf_2$ |
|  | X2 | −0.005 | 10 | 0 | 100 | 0.1 | 0.05 | $Inf_2$ | $Inf_1$ |
| BP | Q1 | −2 | −5 | 0.01 | 0.01 | 0.1 | 0.3 | $Inf_2$ | $Inf_2$ |
|  | Q2 | 10 | 20 | 125 | 125 | 0.075 | 0.03 | $Inf_1$ | $Inf_1$ |
|  | N1 | −0.05 | −0.05 | 0.01 | 0.01 | 0.2 | 0.2 | $Inf_2$ | $Inf_2$ |
|  | N2 | 1 | 2 | 5 | 50 | 0.05 | 0.075 | $Inf_1$ | $Inf_1$ |
|  | X1 | −0.05 | −0.05 | 0.01 | 0.01 | 0.1 | 0.1 | $Inf_2$ | $Inf_2$ |
|  | X2 | 15 | 60 | 150 | 300 | 0.075 | 0.015 | $Inf_1$ | $Inf_1$ |
| CF |  | n/a | 0.002 | 0.002 | 0.001 | 0.001 | 4 | 10 | $Inf_1$ | $Inf_1$ |

IF Influence Function  CF Conformality
BU Biologically Uniform  BP Bioligically Polymorphic
\* unchecked  \*\* checked With reference again to FIG. 2, the next step in the planning system is the Instrument Fitting step 804. The resulting optimized set of radiation beam positions and beam weights, or beam intensities for the radiation beam segments, is fitted into the delivery capabilities of the LINAC apparatus 300 (FIG. 1), after optimization. An iterative process is utilized to account for OF adjustments (Output Factor), the timing of the movement of members, and limitations of simultaneous movements to arrive at control information for the LINAC apparatus 300 (FIG. 1) that represent the optimized plan and can be delivered within the operating limitations of the LINAC apparatus 300 (FIG. 1).

A Strength Normalize step 805 further normalizes the arcs of rotation through which the radiation beam source travels to insure that the tumor receives a consistent radiation dose from each position selected in order to eliminate what are known as "hot" or "cold" regions in the tissue volume being treated. This step may be done by varying the radiation dose rate of the radiation source, and may be accomplished by use of a conventional, simple linear scaling technique.

In the Dose Simulation step 800 the radiation dose to the patient is simulated based upon the control information for LINAC apparatus 300 (FIG. 1). The algorithm used in this step is based upon the Three-Dimensional Modified Path Length technique, as is known in the art. Examples of this algorithm are discussed in the following publications: "Algorithm for Dosimetry of Multiarc Linear Accelerator Stereotactic Radiosurgery," G. Luxton et al., Medical Physics, vol. 18, pp. 1211–1221 (1991); "Dosage Calculations in Radiation Therapy," W. L. Saylor, published by Urban & Schwarzenberg (1979), which publications are incorporated herein by reference.

The Output Process step 807 permits the physician to review the simulated radiation dose information and to approve the radiation plan for patient delivery. After such review and approval, a floppy disk is generated containing the data to control LINAC apparatus 300 (FIG. 1) for the specific radiation delivery case. The data includes instructions for the timing and movement of members, radiation source setup information, and conventional patient information. After the foregoing steps have been accomplished, the Delivery System step 808 is accomplished, wherein the method steps of the conformal radiation therapy method of the present invention are performed as previously described, in order to treat the tumor in the patient.

What is claimed is:

1. A method of determining an optimized radiation beam arrangement for applying radiation to a tumor target volume while minimizing radiation of a structure volume in a patient, comprising the steps of:

using a computer to computationally obtain a proposed radiation beam arrangement;

using a computer to computationally change the proposed radiation beam arrangement iteratively, incorporating a cost function at each iteration to approach correspondence of a CDVH associated with the proposed radiation beam arrangement to a CDVH associated with a predetermined desired dose prescription;

comparing the dose distribution to a prescribed dose for the tumor volume and surrounding tissue structures, and increasing or decreasing radiation beam intensity if the change of the proposed beam arrangement leads to a greater correspondence to the desired dose prescription to obtain an optimized radiation beam arrangement.

2. The method of claim 1, wherein the cost function is obtained by the steps of:

determining a CDVH associated with the desired dose prescription;

assigning zones to each CDVH;

assigning weights to each zone, applicable to the CDVHs associated with both the desired dose prescription and the proposed radiation beam arrangement;

calculating a zone cost for each target and each structure, according to the following formula:

$$INF_1(x, scale, base, offset) = \begin{vmatrix} base\ x - offset^3 + scale\ x, \text{if } x/ \geq offset \\ scale\ x, \text{if } x < offset \end{vmatrix},$$

where x is a given control point value for a given pair CDVH curves;

offset is a predetermined value along an influence curve as a function of x, where the influence curve turns from linear to exponential;

scale is a predetermined value which controls the influence function up to a point along the influence curve at which x=offset; and base is a predetermined value which controls the influence function beyond the point alone the influence curve at which x=offset.

3. The method of claim 1 or 2, wherein the proposed radiation beam arrangement is calculated using simulated annealing radiation therapy planning methods.

4. The method of claim 1 or 2, further comprising the step of applying the optimized radiation beam arrangement to the patient with a conformal radiation therapy apparatus.

5. The method of claim 3, further comprising the step of applying the optimized radiation beam arrangement to the patient with a conformal radiation therapy apparatus.

6. The method of claim 4, further comprising the step of applying the optimized radiation beam arrangement to the patient with a conformal radiation therapy apparatus.

7. The method of claim 1, wherein the CDVH associated with the predetermined desired dose prescription is computationally constructed by the computer based on partial volume data associated with the predetermined desired dose prescription entered into the computer.

8. The method of claim 1, wherein the CDVH associated with the predetermined desired dose prescription is graphically entered into the computer.

9. The method of claim 2, wherein the CDVH associated with the predetermined desired dose prescription is computationally constructed by the computer based on partial volume data associated with the predetermined desired dose.

10. The method of claim 2, wherein the CDVH associated with the predetermined desired dose prescription is graphically entered into the computer.

11. The method of claim 1, wherein the cost function is obtained by the steps of:

determining a CDVH associated with the desired dose prescription;

assigning zones to each CDVH;

assigning weights to each zone, applicable to the CDVHs associated with both the desired dose prescription and the proposed radiation beam arrangement;

calculating a zone cost for each target and each structure, according to the following formula $$INF_2(x, scale, base, offset) =$$

$$\begin{vmatrix} -scale\left[\dfrac{(x-offset)^2}{x-offset+base}\right] + scale(x), \text{if } x \geq offset \\ scale(x), \text{if } x < offset \end{vmatrix}$$

where x is a given control point value for a given pair CDVH curves;

offset is a predetermined value along an influence curve as a functionof x, where the influence curve turns from linear to exponential;

scale is a predetermined value which controls the influence function up to a point along the influence curve at which x=offset; and base is a predetermined value which controls the influence function beyond the point alone the influence curve at which x=offset value.

12. The method of claim 11, wherein the proposed radiation beam arrangement is calculated using simulated annealing radiation therapy planning methods.

13. The method of claim 11, further comprising the step of applying the optimized radiation beam arrangement to the patient with a conformal radiation therapy apparatus.

14. The method of claim 12, further comprising the step of applying the optimized radiation beam arrangement to the patient with a conformal radiation therapy apparatus.

15. The method of claim 13, further comprising the step of applying the optimized radiation beam arrangement to the patient with a conformal radiation therapy apparatus.

16. The method of claim 11, wherein the CDVH associated with the predetermined desired dose prescription is computationally constructed by the computer based on partial volume data associated with the predetermined desired dose.

17. The method of claim 14, wherein the CDVH associated with the predetermined desired dose prescription is graphically entered into the computer.

18. The method of claim 1, 2, or 14 further comprising the step of allowing a radiation limit on the tissue structure to be exceeded by a set amount if such excess allows better conformation to the desired target CDVH curve.

19. The method of claim 1, further comprising providing a user with a range of values to indicate the importance of each object of irradiation to the user.

20. The method of claim 1, further comprising providing a user with a range of values for conformality control.

21. A method of determining an optimized radiation beam arrangement for applying radiation to a tumor target volume while minimizing radiation of a structure volume in a patient, comprising the steps of:

(a) determining a desired CDVH associated with each target and structure;

(b) using a computer to iteratively compare a cost of a radiation beam arrangement proposed during a given iteration to a radiation beam arrangement proposed during the previous iteration based on the relative costs associated with the proposed radiation beam arrangement, the costs being calculated by:

(1) determining a CDVH associated with each target and structure based on the proposed radiation beam arrangement of a given iteration;

(2) assigning cost zones to the desired CDVH and the proposed CDVH of a given iteration associated with each target and structure;

(3) assigning a weight value to each cost zone of each CDVH associated with each target and structure;

(4) for each target and structure, multiplying the weight value of each zone by the quotient of a value representing the area of the zone of the CDVH associated with the proposed radiation beam arrangement and a value representing the area of the zone of the CDVH associated with the desired radiation beam arrangement;

(5) summing the results of step (4) for each zone of each CDVH of each target and structure to obtain a total dosage cost;

(c) increasing or decreasing radiation beam intensity if the change of the proposed beam arrangement leads to a greater correspondence to the desired dose prescription;

(d) allowing a radiation limit on the tissue structure to be exceeded by a set amount if such excess allows better conformation to the desired target CDVH curve; and (e) repeating steps b through d until the proposed radiation beam arrangement has obtained an optimized radiation beam arrangement.

22. The method of claim 21, wherein the proposed radiation beam arrangement is calculated using simulated annealing radiation therapy planning methods.

23. The method of claim 21, further comprising the step of applying the optimized radiation beam arrangement to the patient using a conformal radiation therapy apparatus.

24. The method of claim 22, further comprising the step of applying the optimized radiation beam arrangement to the patient using a conformal radiation therapy apparatus.

25. A method of determining an optimized radiation beam arrangement for applying radiation to a tumor target volume while minimizing radiation of a structure volume in a patient, comprising the steps of:
   using a computer to iteratively obtain a proposed radiation beam arrangement;
   providing a user with a selective range of input values with an indication of the importance of the value in providing an optimized radiation beam arrangement; and
   providing separate parameter profiles depending on the the user's input value selection.

26. The method of claim 25, wherein the input value is an object to be irradiated.

27. The method of claim 25, wherein the input value is in units of conformality control.

28. The method of claim 25, wherein the proposed radiation beam arrangement is changed by changing the beam weights.

29. The method of claim 25, wherein the partial volume data is calculated by the computer based on a CDVH graphically entered into the computer using a pointing device.

30. The method of claim 25, wherein the partial volume data is entered directly into the computer.

31. Apparatus for determining an optimized radiation beam arrangement for applying radiation to a tumor target volume while minimizing radiation of a structure volume in a patient, comprising a computer which is adapted to:
   (a) computationally obtain a proposed radiation beam arrangement,
   (b) computationally change the proposed radiation beam arrangement iteratively to conform to a target CDVH curve,
   (c) incorporate a cost function at each iteration to approach correspondence of partial volume data associated with the proposed radiation beam arrangement to partial volume data associated with a predetermined desired dose prescription,
   (d) reject the change of the proposed radiation beam arrangement if the change of the proposed radiation beam arrangement leads to a lesser correspondence to the desired dose prescription and to accept the change of the proposed radiation beam arrangement if the change of the proposed radiation beam arrangement leads to a greater correspondence to the desired dose prescription to obtain an optimized radiation beam arrangement, and
   (e) exceed the cost function by a set amount if such excess allows better conformation with the target CDHV curve.

32. The apparatus of claim 31, wherein the proposed radiation beam arrangement is changed by changing the beam weights.

33. The apparatus of claim 31, further comprising:
   a conformal radiation therapy apparatus in communication with the computer for applying the optimized radiation beam arrangement to the patient.

34. Apparatus for determining an optimized radiation beam arrangement for applying radiation to a tumor target volume while minimizing radiation of a structure volume in a patient, comprising a computer, including:
   means for computationally obtaining a proposed radiation beam arrangement;
   means for computationally changing the proposed radiation beam arrangement iteratively to conform to a CDHV curve;
   means for incorporating a cost function at each iteration to approach correspondence of partial volume data associated with the proposed radiation beam arrangement to partial volume data associated with a predetermined desired dose prescription;
   means for rejecting the change of the proposed radiation beam arrangement if the change of the proposed radiation beam arrangement leads to a lesser correspondence to the desired dose prescription and accepting the change of the proposed radiation beam arrangement if the change of the proposed radiation beam arrangement leads to a greater correspondence to the desired dose prescription to obtain an optimized radiation beam arrangement; and
   means for adapting the radiation beam arrangement to exceed the cost function by a set amount if such excess allows better conformation with the target CDHV curve.

35. The apparatus of claim 34, wherein the means for computationally changing the proposed radiation beam arrangement includes a means for changing the beam weights.

36. The apparatus of claim 34, further comprising a conformal radiation therapy apparatus in communication with the computer for applying the optimized radiation beam arrangement to the patient.

37. A method of determining an optimized radiation beam arrangement for applying radiation to at least one tumor target volume while minimizing radiation of at least one structure volume in a patient, comprising the steps of:
   determining desired partial volume data for each of the at least one target volume and structure volume associated with a desired dose prescription;
   entering the desired partial volume data into a computer;
   in response to the desired partial volume data, using the computer to computationally approximate desired CDVHs for each of the at least one target and structure associated with the desired dose prescription; and
   using the computer to computationally calculate the optimized radiation beam arrangement associated with the CDVHs approximated by the computer.

38. The method of claim 37, wherein the CDVHs approximated by the computer are approximated by the steps of:
   using the computer to computationally obtain a set of proposed beam weights;
   using the computer to computationally change the set of proposed beam weights iteratively, incorporating a cost function at each iteration to determine a cost of the change to the set of proposed beam weights; and
   rejecting the change to the set of proposed beam weights if the change to the set of proposed beam weights leads to a lesser correspondence to the desired CDVHs and accepting the change to the set of proposed beam weights if the change to the set of proposed beam weights leads to a greater correspondence to the desired CDVHs.

39. The method of claim 38, wherein the optimized radiation beam arrangement is calculated using simulated annealing radiation therapy planning methods.

40. The method of claim 38, further comprising the step of applying the optimized radiation beam arrangement to the patient with a conformal radiation therapy apparatus.

41. The method of claim 38, wherein the desired CDVHs are computationally constructed by the computer based on numerical values representing the partial volume data entered into the computer.

42. The method of claim 37 or 38, wherein the desired CDVHs are computationally constructed by the computer based on numerical values representing the partial volume data entered into the computer.

43. A method of determining an optimized radiation beam arrangement for applying radiation to at least one tumor target volume while minimizing radiation to at least one structure volume in a patient, comprising the steps of:

distinguishing each of the at least one tumor target volume and each of the at least one structure volume by target or structure type;

determining desired partial volume data for each of the at least one target volume and structure volume associated with a desired dose prescription;

entering the desired partial volume data into a computer;

providing a user with a range of values to indicate the importance of objects to be irradiated;

providing the user with a range of conformality control factors; and using the computer to computationally calculate an optimized radiation beam arrangement.

44. The method of claim 43, further comprising the step of applying the optimized radiation beam arrangement to the patient with a conformal radiation therapy apparatus.

45. The method of claim 43, wherein the target or structure types are distinguished as either Biologically Uniform or Biologically Polymorphic.

46. The method of claim 43, wherein the optimized radiation beam arrangement is calculated using different cost function parameters depending on the target or structure type.

* * * * *

(12) INTER PARTES REVIEW CERTIFICATE (2973rd)
United States Patent (10) Number: US 6,393,096 K1
Carol et al. (45) Certificate Issued: Jan. 19, 2023

(54) PLANNING METHOD AND APPARATUS FOR RADIATION DOSIMETRY

(75) Inventors: Mark P. Carol; Richard Nash; Bruce H. Curran; Robert Hill

(73) Assignee: BEST MEDICAL INTERNATIONAL, INC.

Trial Numbers:

IPR2020-00071 filed Oct. 18, 2019
IPR2020-00971 filed May 28, 2020
IPR2020-00072 filed Oct. 18, 2019
IPR2020-00970 filed May 28, 2020

Inter Partes Review Certificate for:

Patent No.: 6,393,096
Issued: May 21, 2002
Appl. No.: 09/320,980
Filed: May 27, 1999

The results of IPR2020-00071 joined with IPR2020-00971; IPR2020-00072 joined with IPR2020-00970 are reflected in this inter partes review certificate under 35 U.S.C. 318(b).

INTER PARTES REVIEW CERTIFICATE
U.S. Patent 6,393,096 K1
Trial No. IPR2020-00071
Certificate Issued Jan. 19, 2023

AS A RESULT OF THE INTER PARTES REVIEW PROCEEDING, IT HAS BEEN DETERMINED THAT:

Claim 18 is found patentable.

Claims 1, 43, 44 and 46 are cancelled.

\* \* \* \* \*